US008946505B2

(12) United States Patent
Frendewey et al.

(10) Patent No.: US 8,946,505 B2
(45) Date of Patent: *Feb. 3, 2015

(54) PROMOTER-REGULATED DIFFERENTIATION-DEPENDENT SELF-DELETING CASSETTE

(71) Applicant: Regeneron Pharmaceuticals, Inc., Tarrytown, NY (US)

(72) Inventors: David Frendewey, New York, NY (US); Guochun Gong, Elmsford, NY (US); Ka-Man Venus Lai, Tarrytown, NY (US); David M. Valenzuela, Yorktown Heights, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/934,829

(22) Filed: Jul. 3, 2013

(65) Prior Publication Data

US 2013/0312129 A1 Nov. 21, 2013

Related U.S. Application Data

(62) Division of application No. 12/856,163, filed on Aug. 13, 2010, now Pat. No. 8,518,392.

(60) Provisional application No. 61/233,974, filed on Aug. 14, 2009.

(51) Int. Cl.
*C12N 15/873* (2010.01)
*A01K 67/027* (2006.01)
*C12N 15/85* (2006.01)
*C12N 15/90* (2006.01)

(52) U.S. Cl.
CPC .......... *C12N 15/873* (2013.01); *A01K 67/0275* (2013.01); *C12N 15/8509* (2013.01); *C12N 15/907* (2013.01); *C12N 15/85* (2013.01); *A01K 2217/07* (2013.01); *A01K 2217/206* (2013.01); *A01K 2227/105* (2013.01); *C12N 2800/30* (2013.01); *C12N 2840/102* (2013.01)
USPC .................................. 800/18; 800/14; 800/21

(58) Field of Classification Search
CPC .......... A01K 67/0275; A01K 2217/07; A01K 2217/206; A01K 2227/105; C12N 15/85; C12N 15/907; C12N 2800/30; C12N 2840/102; C12N 15/873
See application file for complete search history.

(56) References Cited

U.S. PATENT DOCUMENTS

| 6,146,888 | A | 11/2000 | Smith et al. | |
|---|---|---|---|---|
| 7,135,608 | B1 | 11/2006 | O'Gorman et al. | |
| 8,354,389 | B2 | 1/2013 | Frendewey et al. | |
| 8,518,392 | B2 * | 8/2013 | Frendewey et al. | 424/93.21 |
| 8,697,851 | B2 | 4/2014 | Frendewey et al. | |
| 2008/0295192 | A1 | 11/2008 | Thomas et al. | |
| 2011/0041196 | A1 | 2/2011 | Frendewey et al. | |
| 2011/0041197 | A1 | 2/2011 | Frendewey et al. | |
| 2013/0095565 | A1 | 4/2013 | Frendewey et al. | |
| 2013/0312128 | A1 | 11/2013 | Frendewey et al. | |
| 2014/0189900 | A1 | 7/2014 | Frendewey et al. | |
| 2014/0199761 | A1 | 7/2014 | Frendewey et al. | |

FOREIGN PATENT DOCUMENTS

| EP | 0695351 | 8/1999 |
|---|---|---|
| WO | WO-9520042 | 7/1995 |
| WO | WO-2005078098 | 8/2005 |
| WO | WO-2007000668 | 1/2007 |
| WO | WO-2007149246 | 12/2007 |
| WO | WO-2008112226 | 9/2008 |
| WO | WO-2008128144 | 10/2008 |
| WO | WO-2009114400 | 9/2009 |
| WO | WO/2011/020005 | 2/2011 |
| WO | WO/2011/020014 | 2/2011 |

OTHER PUBLICATIONS

Clark et al. Nature Reviews: 4: 825-833, 2003.*
U.S. Appl. No. 13/692,764, Non-Final Office Action mailed Apr. 8, 2013.
U.S. Appl. No. 13/692,764, Final Office Action mailed Sep. 9, 2013.
U.S. Appl. No. 12/856,126, Non-Final Office Action mailed Mar. 30, 2012.
U.S. Appl. No. 12/856,126, Final Office Action mailed Aug. 7, 2012.
U.S. Appl. No. 13/934,815, Requirement for Restriction/Election mailed Jan. 17, 2014.
U.S. Appl. No. 13/934,815, Non-Final Office Action mailed Mar. 26, 2014.
U.S. Appl. No. 12/856,163, Requirement for Restriction/Election mailed Feb. 13, 2012.
U.S. Appl. No. 12/856,163, Non-Final Office Action mailed Jul. 6, 2012.
U.S. Appl. No. 12/856,163, Final Office Action mailed Jan. 24, 2013.
U.S. Appl. No. 14/176,484, Requirement for Restriction Election mailed Jun. 10, 2014.
U.S. Appl. No. 14/176,484, Non-Final Office Action mailed Sep. 9, 2014.

(Continued)

*Primary Examiner* — Doug Schultz
(74) *Attorney, Agent, or Firm* — Yong-Jin Choi; Tor Smeland; Alston & Bird LLP

(57) ABSTRACT

Targeting constructs and methods of using them are provided for differentiation-dependent modification of nucleic acid sequences in cells and in non-human animals. Targeting constructs comprising a promoter operably linked to a recombinase are provided, wherein the promoter drives transcription of the recombinase in an differentiated cell but not an undifferentiated cell. Promoters include Blimp1, Prm1, Gata6, Gata4, Igf2, Lhx2, Lhx5, and Pax3. Targeting constructs with a cassette flanked on both sides by recombinase sites can be removed using a recombinase gene operably linked to a 3'-UTR that comprises a recognition site for an miRNA that is transcribed in undifferentiated cells but not in differentiated cells. The constructs may be included in targeting vectors, and can be used to automatically modify or excise a selection cassette from an ES cell, a non-human embryo, or a non-human animal.

11 Claims, 7 Drawing Sheets

(56) References Cited

OTHER PUBLICATIONS

Bunting et al., "Targeting genes for self-excision in the germ line," Genes and Development, 13: 1524-1528, 1999.

International Search Report of International Application No. PCT/US2010/045464, mailed Nov. 17, 2010.

John et al., "Blimp1: A conserved transcriptional repressor critical for differentiation of m any tissues," Experimental Cell Research, 315: 1077-1084, 2009.

Mahonen et al., "Optimized self-excising Cre-expression cassette for mammalian cells," Biochemical and Biophysical Research Communications, 320: 366-371, 2004.

Matsumura et al., "Lineage-specific cell disruption in living mice by Cre-mediated expression of diphtheria toxin A chain," Biochemical and Biophysical Research Communications, 321: 275-279, 2004.

Schmidt et al., "Illegitimate Cre-dependent chromosome rearrangements in transgenic mouse spermatids," Proc. Natl. Acad. Sci. USA, 97(25): 13702-13707, 2000.

Silver et al., "Self-Excising Retroviral Vectors Encoding the Cre-Recombinase Overcome Cre-Mediated Cellular Toxicity," Molecular Cell, 8: 233-243, 2001.

Tunyaplin et al., "Characterization of the B lymphocyte-induced maturation protein-1 (Blimp-1) gene, mRNA isoforms and basal promoter," Nucleic Acids Research, 28(24): 4846-4855, 2000.

Von Melchner et al., "Engineering of ES Cell Genomes with Recombinase Systems," Handbook of Stem Cells, 1: 609-622, 2004.

Wang et al., "The Blimp-1 gene regulatory region directs EGFP expression in multiple hematopoietic lineages and testis in mice," Transgenic Research, 17: 193-203, 2008.

Zambrowicz et al., "Analysis of the mouse protamine 1 promoter in transgenic mice," Proc. Natl. Acad. Sci. USA, 90: 5071-5075, 1993.

Zambrowicz et al., "Testis-Specific and Ubiquitous Proteins Bind to Functionally Important Regions of the Mouse Protamine-1 Promoter," Biology of Reproduction, 50: 65-72, 1994.

Brown et ano., "Exploiting and antagonizing microRNA regulation for therapeutic and experimental applications," *Nat Rev Genet.* 10(8): 578-585, Aug. 1, 2009.

Brown et al., "Endogenous microRNA can be broadly exploited to regulate transgene expression according to tissue, lineage and differentiation state," *Nature Biotechnology*, 25(12): 1457-1467, Nov. 16, 2007.

Gentner et al., "Exploiting microRNA expression profiles for lineage- and differentiation state-specific transgene expression in hematopoietic, neural and embryonic stem cells," *Blood Cells, Molecules and Diseases*, 40(2): 267, Feb. 12, 2008.

Gu et al., "Novel microRNA candidates and miRNA-mRNA pairs in embryonic stem (ES) cells," *Plos One*, 3(7) E2548: 1-16, Jul. 2, 2008.

Houbaviy et al., "Embryonic Stem Cell-Specific MicroRNAs," *Developmental Cell*, 5(2): 351-358, 2003.

Houbaviy et al., Characterization of a highly variable eutherian microRNA gene, *RNA*, 11(8): 1245-1257, Aug. 1, 2005.

International Search Report of International Application No. PCT/US2010/045455, mailed Dec. 3, 2010.

Landgraf, P., et al., "A Mammalian microRNA Expression Atlas Based on Small RNA Library Sequencing," *Cell* 129: 1401-1414, 2007.

Marson, et al., "Connecting microRNA Genes to the Core Transcriptional Regulatory Circuitry of Embryonic Stem Cells," *Cell*, 134: 521-533, 2008.

\* cited by examiner miRNAs Similar to 292-5p

| | | | | | | | | | 10 | | | | | | | 20 | | | | | |
|---|---|---|---|---|---|---|---|---|---|---|---|---|---|---|---|---|---|---|---|---|---|
| 292-5p | A | C | U | C | A | A | A | C | - | U | G | G | G | G | G | C | - | U | C | U | U | U | G |
| 290-5p | A | C | U | C | A | A | A | C | - | U | A | U | G | G | G | G | G | C | A | C | U | U | U | - |
| 291a-5p | C | A | U | C | A | A | A | G | - | U | G | G | A | G | G | C | C | C | U | C | U | C | U | - |
| 291b-5p | G | A | U | C | A | A | A | G | - | U | G | G | A | G | G | C | C | C | U | C | U | C | C | - |
| 293* | A | C | U | C | A | A | A | C | - | U | G | U | G | U | G | A | - | C | A | U | U | U | U | G |
| 294* | A | C | U | C | A | A | A | A | - | U | G | G | A | G | G | C | C | C | U | A | U | C | U | - |
| 295* | A | C | U | C | A | A | A | U | - | G | U | G | G | G | G | C | A | C | A | C | U | U | C | - |
| 302a* | A | C | U | U | A | A | A | C | G | U | G | G | U | U | G | U | A | C | U | U | G | C | - | - |
| 302b* | A | C | U | U | U | A | A | C | A | U | G | G | G | A | A | U | G | C | U | U | U | C | U | - |
| 302c* | G | C | U | U | U | A | A | C | A | U | G | G | G | G | U | U | A | C | C | U | G | C | - | - |
| 17* | A | C | U | G | C | A | G | U | G | A | G | G | G | C | A | C | U | U | G | U | A | G | - | - |
| 18* | A | C | U | G | C | C | C | U | A | A | G | U | G | C | U | C | C | U | U | C | U | G | - | - |
| 20a* | A | C | U | G | C | A | U | U | A | C | G | A | G | C | A | C | U | U | A | A | A | G | - | - | miRNAs Similar to 292-3p

| | | | | | | | | | | 10 | | | | | | | 20 | | | | | |
|---|---|---|---|---|---|---|---|---|---|---|---|---|---|---|---|---|---|---|---|---|---|---|
| 292-3p | - | A | A | A | G | U | G | C | C | G | C | C | A | G | G | U | U | U | U | G | A | G | U | G | U |
| 290-3p | - | A | A | A | G | U | G | C | C | G | C | C | U | A | G | U | U | U | U | A | A | G | C | C | C |
| 291a-3p | - | A | A | A | G | U | G | C | U | U | C | C | A | C | - | - | U | U | U | G | U | G | U | G | C |
| 291b-3p | - | A | A | A | G | U | G | C | A | U | C | C | A | U | - | - | U | U | U | G | U | U | U | G | U |
| 293 | - | - | - | A | G | U | G | C | C | G | C | A | G | A | G | U | U | U | G | U | A | G | U | G | U |
| 294 | - | A | A | A | G | U | G | C | U | U | C | C | C | U | - | - | U | U | U | G | U | G | U | G | U |
| 295 | - | A | A | A | G | U | G | C | U | A | C | U | A | C | U | - | U | U | U | G | A | G | U | C | U |
| 302a | - | U | A | A | G | U | G | C | U | U | C | C | A | U | G | - | U | U | U | U | G | G | U | G | A |
| 302b | - | U | A | A | G | U | G | C | U | U | C | C | A | U | G | - | U | U | U | U | A | G | U | A | G |
| 302c | - | - | A | A | G | U | G | C | U | U | C | C | A | U | G | - | U | U | U | C | A | G | U | G | G |
| 302d | - | U | A | A | G | U | G | C | U | U | C | C | A | U | G | - | U | U | U | G | A | G | U | G | U |
| 367 | - | - | A | A | U | U | G | C | A | C | U | U | U | A | G | - | C | A | A | U | G | G | U | G | A |
| 17 | C | A | A | A | G | U | G | C | U | U | A | C | A | G | - | - | U | G | C | A | G | G | U | A | G |
| 18a | U | A | A | G | G | U | G | C | A | U | C | U | A | G | - | - | U | G | C | A | G | A | U | A | G |
| 20a | U | A | A | A | G | U | G | C | U | U | A | U | A | G | - | - | U | G | C | A | G | G | U | A | G |

FIG. 2

```
S1  5'-CTAGATAAACACTCAAAAACCTGGGCGGCACTTTTTCGAAACACTCAAAAACCTGGGCGGCACTTTACGCGT-3'
                      <-----miR-292-3p target----->        <-----miR-292-3p target----->
(SEQ. ID NO:57)
                        +
AS1 3'-TATTTGTGAGTTTTTGGACCGCCGTGAAAAAGCTTTGTGAGTTTTTGGACCGCCGTGAAA-5' (SEQ. ID NO:58)
                        ↓ anneal
    Nhe I     <-----miR-292-3p target----->        <-----miR-292-3p target----->  Mlu I
S1  5'-CTAGATAAACACTCAAAAACCTGGGCGGCACTTTTTCGAAACACTCAAAAACCTGGGCGGCACTTTACGCGT-3'
       ||||||||||||||||||||||||||||||||||||||||||||||||||||||||||||||||
AS1    3'-TATTTGTGAGTTTTTGGACCGCCGTGAAAAAGCTTTGTGAGTTTTTGGACCGCCGTGAAA-5'

<-----miR-292-3p target----->
S2  5'-ACACTCAAAAACCTGGGCGGCACTTTATGCATACACTCAAAAACCTGGGCGGCACTTTC-3'  (SEQ. ID NO:59)
                                                 <-----miR-292-3p target----->
AS2 3'-TGCGCATGTGAGTTTTGGACCGCCGTGAAATACGTATGTGAGTTTTGGACCGCCGTGAAAGGGCC-5'
(SEQ ID NO:60)
                        ↓ anneal
              <-----miR-292-3p target----->        <-----miR-292-3p target----->
S2     5'-ACACTCAAAAACCTGGGCGGCACTTTATGCATACACTCAAAAACCTGGGCGGCACTTTC-3'
          ||||||||||||||||||||||||||||||||||||||||||||||||||||||||||||||||
AS2 3'-TGCGCATGTGAGTTTTGGACCGCCGTGAAATACGTATGTGAGTTTTGGACCGCCGTGAAAGGGCC-5'
    Mlu I                                                               Xma I
```

FIG. 3

SEQUENCE LISTING

<160> NUMBER OF SEQ ID NOS: 60

<210> SEQ ID NO 1
<211> LENGTH: 680
<212> TYPE: DNA
<213> ORGANISM: Artificial Sequence
<220> FEATURE:
<223> OTHER INFORMATION: Synthetic

<400> SEQUENCE: 1

```
ccagtagcag cacccacgtc caccttctgt ctagtaatgt ccaacacctc cctcagtcca      60
aacactgctc tgcatccatg tggctcccat ttatacctga agcacttgat ggggcctcaa     120
tgttttacta gagcccaccc ccctgcaact ctgagaccct ctggatttgt ctgtcagtgc     180
ctcactgggg cgttggataa tttcttaaaa ggtcaagttc cctcagcagc attctctgag     240
cagtctgaag atgtgtgctt ttcacagttc aaatccatgt ggctgtttca cccacctgcc     300
tggccttggg ttatctatca ggacctagcc tagaagcagg tgtgtggcac ttaacaccta     360
agctgagtga ctaactgaac actcaagtgg atgccatctt tgtcacttct tgactgtgac     420
acaagcaact cctgatgcca aagccctgcc caccctctc atgcccatat ttggacatgg     480
tacaggtcct cactggccat ggtctgtgag gtcctggtcc tctttgactt cataattcct     540
aggggccact agtatctata agaggaagag ggtgctggct cccaggccac agcccacaaa     600
attccacctg ctcacaggtt ggctggctcg acccaggtgg tgtcccctgc tctgagccag     660
ctcccggcca agccagcacc                                                 680
```

<210> SEQ ID NO 2
<211> LENGTH: 1052
<212> TYPE: DNA
<213> ORGANISM: Artificial Sequence
<220> FEATURE:
<223> OTHER INFORMATION: Synthetic

<400> SEQUENCE: 2

```
tgccatcatc acaggatgtc cttccttctc cagaagacag actggggctg aaggaaaagc      60
cggccaggct cagaacgagc cccactaatt actgcctcca acagctttcc actcactgcc     120
cccagcccaa catcccctt ttaactggga agcattccta ctctccattg tacgcacacg      180
ctcggaagcc tggctgtggg tttgggcatg agaggcaggg acaacaaaac cagtatatat     240
gattataact ttttcctgtt tccctatttc caaatggtcg aaaggaggaa gttaggtcta     300
cctaagctga atgtattcag ttagcaggag aaatgaaatc ctatacgttt aatactagag     360
gagaaccgcc ttagaatatt tatttcattg gcaatgactc caggactaca cagcgaaatt     420
gtattgcatg tgctgccaaa atactttagc tctttccttc gaagtacgtc ggatcctgta     480
attgagacac cgagtttagg tgactagggt tttcttttga ggaggagtcc cccacccgc     540 cccgctctgc cgcgacagga agctagcgat ccggaggact tagaatacaa tcgtagtgtg     600
ggtaaacatg gagggcaagc gcctgcaaag ggaagtaaga agattcccag tccttgttga    660
aatccatttg caaacagagg aagctgccgc gggtcgcagt cggtgggggg aagccctgaa     720
ccccacgctg cacggctggg ctggccaggt gcggccacgc cccatcgcg gcggctggta     780 ggagtgaatc agaccgtcag tattggtaaa gaagtctgcg gcagggcagg gaggggaag     840 agtagtcagt cgctcgctca ctcgctcgct cgcacagaca ctgctgcagt gacactcggc     900
cctccagtgt cgcggagacg caagagcagc gcgcagcacc tgtccgcccg gagcgagccc     960
ggcccgcggc cgtagaaaag gagggaccgc cgaggtgcgc gtcagtactg ctcagcccgg    1020
```
cagggacgcg ggaggatgtg gactgggtgg ac            1052

<210> SEQ ID NO 3
<211> LENGTH: 2008
<212> TYPE: DNA
<213> ORGANISM: Artificial Sequence
<220> FEATURE:
<223> OTHER INFORMATION: Synthetic

<400> SEQUENCE: 3

| | |
|---|---:|
| gtggtgctga ctcagcatcg gttaataaac cctctgcagg aggctggatt tcttttgttt | 60 |
| aattatcact tggacctttc tgagaactct taagaattgt tcattcgggt ttttttgttt | 120 |
| tgttttggtt tggtttttttt gggtttttttt tttttttttt ttttttggttt ttggagacag | 180 |
| ggtttctctg tatatagccc tggcacaaga gcaagctaac agcctgtttc ttcttggtgc | 240 |
| tagcgccccc tctggcagaa aatgaaataa caggtggacc tacaaccccc ccccccccc | 300 |
| ccagtgtatt ctactcttgt ccccggtata aatttgattg ttccgaacta cataaattgt | 360 |
| agaaggattt tttagatgca catatcattt tctgtgatac cttccacaca cccctccccc | 420 |
| ccaaaaaaat ttttctggga aagtttcttg aaaggaaaac agaagaacaa gcctgtcttt | 480 |
| atgattgagt tgggcttttg ttttgctgtg tttcatttct tcctgtaaac aaatactcaa | 540 |
| atgtccactt cattgtatga ctaagttggt atcattaggt tgggtctggg tgtgtgaatg | 600 |
| tgggtgtgga tctggatgtg ggtgggtgtg tatgccccgt gtgtttagaa tactagaaaa | 660 |
| gataccacat cgtaaacttt tgggagagat gattttaaaa atggggtg ggggtgaggg | 720 |
| gaacctgcga tgaggcaagc aagataaggg gaagacttga gtttctgtga tctaaaaagt | 780 |
| cgctgtgatg ggatgctggc tataaatggg cccttagcag cattgtttct gtgaattgga | 840 |
| ggatccctgc tgaaggcaaa agaccattga aggaagtacc gcatctggtt tgttttgtaa | 900 |
| tgagaagcag gaatgcaagg tccacgctct taataataaa caaacaggac attgtatgcc | 960 |
| atcatcacag gatgtccttc cttctccaga agacagactg gggctgaagg aaaagccggc | 1020 |
| caggctcaga acgagcccca ctaattactg cctccaacag cttccactc actgcccca | 1080 |
| gcccaacatc cccttttaa ctgggaagca ttcctactct ccattgtacg cacacgctcg | 1140 |
| gaagcctggc tgtgggtttg ggcatgagag gcagggacaa caaaaccagt atatatgatt | 1200 |
| ataactttt cctgtttccc tatttccaaa tggtcgaaag gaggaagtta ggtctaccta | 1260 |
| agctgaatgt attcagttag caggagaaat gaaatcctat acgtttaata ctagaggaga | 1320 |
| accgccttag aatatttatt tcattggcaa tgactccagg actacacagc gaaattgtat | 1380 |
| tgcatgtgct gccaaaatac tttagctctt ccttcgaag tacgtcggat cctgtaattg | 1440 |
| agacaccgag tttaggtgac tagggttttc ttttgaggag gagtccccca ccccgccccg | 1500 |
| ctctgccgcg acaggaagct agcgatccgg aggacttaga atacaatcgt agtgtgggta | 1560 |
| aacatggagg gcaagcgcct gcaaagggaa gtaagaagat tcccagtcct tgttgaaatc | 1620 |
| catttgcaaa cagaggaagc tgccgcgggt cgcagtcggt gggggaagc cctgaacccc | 1680 |
| acgctgcacg gctgggctgg ccaggtgcgg ccacgccccc atcgcggcgg ctggtaggag | 1740 |
| tgaatcagac cgtcagtatt ggtaaagaag tctgcgcag gcagggagg gggaagagta | 1800 |
| gtcagtcgct cgctcactcg ctcgctcgca cagacactgc tgcagtgaca ctcggccctc | 1860 |
| cagtgtcgcg gagacgcaag agcagcgcgc agcacctgtc cgcccggagc gagcccggcc | 1920 |
| cgcggccgta gaaaaggagg gaccgccgag gtgcgcgtca gtactgctca gcccggcagg | 1980 |

```
gacgcgggag gatgtggact gggtggac                                      2008
```

<210> SEQ ID NO 4
<211> LENGTH: 23
<212> TYPE: RNA
<213> ORGANISM: Mus musculus

<400> SEQUENCE: 4

```
caaagugcuu acagugcagg uag                                             23
```

<210> SEQ ID NO 5
<211> LENGTH: 22
<212> TYPE: RNA
<213> ORGANISM: Mus musculus

<400> SEQUENCE: 5

```
uaaggugcau cuagugcaga ua                                              22
```

<210> SEQ ID NO 6
<211> LENGTH: 23
<212> TYPE: RNA
<213> ORGANISM: Mus musculus

<400> SEQUENCE: 6

```
uaaggugcau cuagugcugu uag                                             23
```

<210> SEQ ID NO 7
<211> LENGTH: 23
<212> TYPE: RNA
<213> ORGANISM: Mus musculus

<400> SEQUENCE: 7

```
ugugcaaauc caugcaaaac uga                                             23
```

<210> SEQ ID NO 8
<211> LENGTH: 23
<212> TYPE: RNA
<213> ORGANISM: Mus musculus

<400> SEQUENCE: 8

```
uaaagugcuu auagugcagg uag                                             23
```

<210> SEQ ID NO 9
<211> LENGTH: 23
<212> TYPE: RNA
<213> ORGANISM: Mus musculus

<400> SEQUENCE: 9

```
caaagugcuc auagugcagg uag                                             23
```

<210> SEQ ID NO 10
<211> LENGTH: 22
<212> TYPE: RNA
<213> ORGANISM: Mus musculus

<400> SEQUENCE: 10

```
uagcuuauca gacugauguu ga                                              22
```

<210> SEQ ID NO 11
<211> LENGTH: 21
<212> TYPE: RNA
<213> ORGANISM: Mus musculus

<400> SEQUENCE: 11

-continued uauugcacuu gucccggccu g                                                    21

<210> SEQ ID NO 12
<211> LENGTH: 23
<212> TYPE: RNA
<213> ORGANISM: Mus musculus

<400> SEQUENCE: 12
caaagugcug uucgugcagg uag                                                  23

<210> SEQ ID NO 13
<211> LENGTH: 23
<212> TYPE: RNA
<213> ORGANISM: Mus musculus

<400> SEQUENCE: 13
uuuggcacua gcacauuuuu gcu                                                  23

<210> SEQ ID NO 14
<211> LENGTH: 23
<212> TYPE: RNA
<213> ORGANISM: Mus musculus

<400> SEQUENCE: 14
caaagugcua acagugcagg uag                                                  23

<210> SEQ ID NO 15
<211> LENGTH: 22
<212> TYPE: RNA
<213> ORGANISM: Mus musculus

<400> SEQUENCE: 15
cagugcaaug uuaaaagggc au                                                   22

<210> SEQ ID NO 16
<211> LENGTH: 22
<212> TYPE: RNA
<213> ORGANISM: Mus musculus

<400> SEQUENCE: 16
uauagggauu ggagccgugg cg                                                   22

<210> SEQ ID NO 17
<211> LENGTH: 23
<212> TYPE: RNA
<213> ORGANISM: Mus musculus

<400> SEQUENCE: 17
uguaguguuu ccuacuuuau gga                                                  23

<210> SEQ ID NO 18
<211> LENGTH: 22
<212> TYPE: RNA
<213> ORGANISM: Mus musculus

<400> SEQUENCE: 18
aacauucaac cugucgguga gu                                                   22

<210> SEQ ID NO 19
<211> LENGTH: 22
<212> TYPE: RNA
<213> ORGANISM: Mus musculus

```
<400> SEQUENCE: 19
gugaauuacc gaagggccau aa                                          22

<210> SEQ ID NO 20
<211> LENGTH: 22
<212> TYPE: RNA
<213> ORGANISM: Mus musculus

<400> SEQUENCE: 20
uaacagucuc cagucacggc ca                                          22

<210> SEQ ID NO 21
<211> LENGTH: 22
<212> TYPE: RNA
<213> ORGANISM: Mus musculus

<400> SEQUENCE: 21
caucaaagug gaggcccucu cu                                          22

<210> SEQ ID NO 22
<211> LENGTH: 24
<212> TYPE: RNA
<213> ORGANISM: Mus musculus

<400> SEQUENCE: 22
aaagugccgc cuaguuuaa gccc                                         24

<210> SEQ ID NO 23
<211> LENGTH: 22
<212> TYPE: RNA
<213> ORGANISM: Mus musculus

<400> SEQUENCE: 23
acucaaacug ggggcucuuu ug                                          22

<210> SEQ ID NO 24
<211> LENGTH: 22
<212> TYPE: RNA
<213> ORGANISM: Mus musculus

<400> SEQUENCE: 24
aaagugcuuc cacuuugugu gc                                          22

<210> SEQ ID NO 25
<211> LENGTH: 22
<212> TYPE: RNA
<213> ORGANISM: Mus musculus

<400> SEQUENCE: 25
aaagugcauc cauuuuguuu gu                                          22

<210> SEQ ID NO 26
<211> LENGTH: 24
<212> TYPE: RNA
<213> ORGANISM: Mus musculus

<400> SEQUENCE: 26
aaagugccgc cagguuuuga gugu                                        24

<210> SEQ ID NO 27
<211> LENGTH: 22
<212> TYPE: RNA
<213> ORGANISM: Mus musculus
```

```
<400> SEQUENCE: 27
agugccgcag aguuuguagu gu                                              22

<210> SEQ ID NO 28
<211> LENGTH: 22
<212> TYPE: RNA
<213> ORGANISM: Mus musculus

<400> SEQUENCE: 28
aaagugcuuc ccuuuugugu gu                                              22

<210> SEQ ID NO 29
<211> LENGTH: 23
<212> TYPE: RNA
<213> ORGANISM: Mus musculus

<400> SEQUENCE: 29
aaagugcuac uacuuuugag ucu                                             23

<210> SEQ ID NO 30
<211> LENGTH: 23
<212> TYPE: RNA
<213> ORGANISM: Mus musculus

<400> SEQUENCE: 30
uaagugcuuc cauguuuugg uga                                             23

<210> SEQ ID NO 31
<211> LENGTH: 23
<212> TYPE: RNA
<213> ORGANISM: Mus musculus

<400> SEQUENCE: 31
uaagugcuuc cauguuuuag uag                                             23

<210> SEQ ID NO 32
<211> LENGTH: 22
<212> TYPE: RNA
<213> ORGANISM: Mus musculus

<400> SEQUENCE: 32
aagugcuucc auguuucagu gg                                              22

<210> SEQ ID NO 33
<211> LENGTH: 23
<212> TYPE: RNA
<213> ORGANISM: Mus musculus

<400> SEQUENCE: 33
uaagugcuuc cauguuugag ugu                                             23

<210> SEQ ID NO 34
<211> LENGTH: 22
<212> TYPE: RNA
<213> ORGANISM: Mus musculus

<400> SEQUENCE: 34
aauugcacuu uagcaauggu ga                                              22

<210> SEQ ID NO 35
<211> LENGTH: 22
<212> TYPE: RNA
```

```
<213> ORGANISM: Mus musculus

<400> SEQUENCE: 35
gccugcuggg guggaaccug gu                                            22

<210> SEQ ID NO 36
<211> LENGTH: 22
<212> TYPE: RNA
<213> ORGANISM: Mus musculus

<400> SEQUENCE: 36
gcucgacuca ugguuugaac ca                                            22

<210> SEQ ID NO 37
<211> LENGTH: 22
<212> TYPE: RNA
<213> ORGANISM: Mus musculus

<400> SEQUENCE: 37
ugaaacauac acgggaaacc uc                                            22

<210> SEQ ID NO 38
<211> LENGTH: 22
<212> TYPE: RNA
<213> ORGANISM: Mus musculus

<400> SEQUENCE: 38
aaaggcuagg cucacaacca aa                                            22

<210> SEQ ID NO 39
<211> LENGTH: 22
<212> TYPE: RNA
<213> ORGANISM: Mus musculus

<400> SEQUENCE: 39
agagaaaccc ugucucaaaa aa                                            22

<210> SEQ ID NO 40
<211> LENGTH: 19
<212> TYPE: RNA
<213> ORGANISM: Mus musculus

<400> SEQUENCE: 40
ggaggcagag gcaggagga                                                19

<210> SEQ ID NO 41
<211> LENGTH: 21
<212> TYPE: RNA
<213> ORGANISM: Mus musculus

<400> SEQUENCE: 41
cuccuucacc cgggcgguac c                                             21

<210> SEQ ID NO 42
<211> LENGTH: 21
<212> TYPE: RNA
<213> ORGANISM: Mus musculus

<400> SEQUENCE: 42
cuuccgcccg gccggguguc g                                             21

<210> SEQ ID NO 43
<211> LENGTH: 18
```

```
<212> TYPE: RNA
<213> ORGANISM: Mus musculus

<400> SEQUENCE: 43
aucucgcugg ggccucca                                                    18

<210> SEQ ID NO 44
<211> LENGTH: 21
<212> TYPE: RNA
<213> ORGANISM: Mus musculus

<400> SEQUENCE: 44
gugaggacug gggaggugga g                                                21

<210> SEQ ID NO 45
<211> LENGTH: 22
<212> TYPE: RNA
<213> ORGANISM: Mus musculus

<400> SEQUENCE: 45
ggccgcccuc ucugguccuu ca                                               22

<210> SEQ ID NO 46
<211> LENGTH: 22
<212> TYPE: RNA
<213> ORGANISM: Mus musculus

<400> SEQUENCE: 46
acucaaacua uggggcacu uu                                                22

<210> SEQ ID NO 47
<211> LENGTH: 22
<212> TYPE: RNA
<213> ORGANISM: Mus musculus

<400> SEQUENCE: 47
gaucaaagug gaggcccucu cc                                               22

<210> SEQ ID NO 48
<211> LENGTH: 22
<212> TYPE: RNA
<213> ORGANISM: Mus musculus

<400> SEQUENCE: 48
acucaaacug ugugacauuu ug                                               22

<210> SEQ ID NO 49
<211> LENGTH: 22
<212> TYPE: RNA
<213> ORGANISM: Mus musculus

<400> SEQUENCE: 49
acucaaaaug gaggcccuau cu                                               22

<210> SEQ ID NO 50
<211> LENGTH: 22
<212> TYPE: RNA
<213> ORGANISM: Mus musculus

<400> SEQUENCE: 50
acucaaaugu ggggcacacu uc                                               22

<210> SEQ ID NO 51
```

```
<211> LENGTH: 22
<212> TYPE: RNA
<213> ORGANISM: Mus musculus

<400> SEQUENCE: 51
acuuaaacgu gguuguacuu gc                                              22

<210> SEQ ID NO 52
<211> LENGTH: 23
<212> TYPE: RNA
<213> ORGANISM: Mus musculus

<400> SEQUENCE: 52
acuuuaacau gggaaugcuu ucu                                             23

<210> SEQ ID NO 53
<211> LENGTH: 22
<212> TYPE: RNA
<213> ORGANISM: Mus musculus

<400> SEQUENCE: 53
gcuuuaacau gggguuaccu gc                                              22

<210> SEQ ID NO 54
<211> LENGTH: 22
<212> TYPE: RNA
<213> ORGANISM: Mus musculus

<400> SEQUENCE: 54
acugcaguga gggcacuugu ag                                              22

<210> SEQ ID NO 55
<211> LENGTH: 22
<212> TYPE: RNA
<213> ORGANISM: Mus musculus

<400> SEQUENCE: 55
acugcccuaa gugcuccuuc ug                                              22

<210> SEQ ID NO 56
<211> LENGTH: 22
<212> TYPE: RNA
<213> ORGANISM: Mus musculus

<400> SEQUENCE: 56
acugcauuac gagcacuuaa ag                                              22

<210> SEQ ID NO 57
<211> LENGTH: 68
<212> TYPE: DNA
<213> ORGANISM: Artificial Sequence
<220> FEATURE:
<223> OTHER INFORMATION: Synthetic

<400> SEQUENCE: 57
ctagataaac actcaaaacc tggcggcact ttttcgaaac actcaaaacc tggcggcact    60
ttacgcgt                                                              68

<210> SEQ ID NO 58
<211> LENGTH: 58
<212> TYPE: DNA
<213> ORGANISM: Artificial Sequence
<220> FEATURE:
<223> OTHER INFORMATION: Synthetic
```

```
<400> SEQUENCE: 58
tatttgtgag ttttggaccg ccgtgaaaaa gctttgtgag ttttggaccg ccgtgaaa         58

<210> SEQ ID NO 59
<211> LENGTH: 55
<212> TYPE: DNA
<213> ORGANISM: Artificial Sequence
<220> FEATURE:
<223> OTHER INFORMATION: Synthetic

<400> SEQUENCE: 59
acactcaaaa cctggcggca ctttatgcat acactcaaaa cctggcggca ctttc           55

<210> SEQ ID NO 60
<211> LENGTH: 65
<212> TYPE: DNA
<213> ORGANISM: Artificial Sequence
<220> FEATURE:
<223> OTHER INFORMATION: Synthetic

<400> SEQUENCE: 60
tgcgcatgtg agttttggac cgccgtgaaa tacgtatgtg agttttggac cgccgtgaaa      60
gggcc                                                                  65
```

PROMOTER-REGULATED DIFFERENTIATION-DEPENDENT SELF-DELETING CASSETTE

CROSS-REFERENCE TO RELATED APPLICATIONS

This application is a divisional of U.S. patent application Ser. No. 12/856,163, filed 13 Aug. 2010, which claims the benefit under 35 USC §119(e), and is a nonprovisional, of U.S. Provisional Patent Application Ser. No. 61/233,974, filed 14 Aug. 2009, which applications are hereby incorporated by reference in their entirety.

FIELD OF INVENTION

The invention relates to nucleic acid constructs comprising cassettes for deleting nucleic acid sequences from genetically modified cells and animals, in particular for use in connection with targeting vectors in order to delete nucleic acid sequences introduced into a cell or an animal using a targeting vector.

BACKGROUND

Targeted gene modification in the mouse (commonly referred to as knockout mouse technology because the goal of many of the modifications is to abolish, or knock out, target gene function) is the most effective method for discovery of mammalian gene function in live animals and for creating genetic models of human disease. Knockout mouse creation typically begins by introducing a targeting vector into mouse embryonic stem (ES) cells. The targeting vector is a linear piece of DNA comprising a selection or marker gene (e.g., for drug selection) flanked by mouse DNA sequences—the so-called homology arms—that are similar or identical to the sequences at the target gene and which promote integration into the genomic DNA at the target gene locus by homologous recombination. To create a mouse with an engineered genetic modification, targeted ES cells are introduced into mouse embryos, for example pre-morula stage (e.g., 8-cell stage) or blastocyst stage embryos, and then the embryos are implanted in the uterus of a surrogate mother (e.g., a pseudopregnant mouse) that will give birth to pups that are partially or fully derived from the genetically modified ES cells. After growing to sexual maturity and breeding with wild type mice some of the pups will transmit the modified gene to their progeny, which will be heterozygous for the mutation. Interbreeding of heterozygous mice will produce progeny that are homozygous for the modified allele and are commonly referred to as knockout mice.

The initial step of creating gene-targeted ES cells is a rare event. Only a small portion of ES cells exposed to the targeting vector will incorporate the vector into their genomes, and only a small fraction of such cells will undergo accurate homologous recombination at the target locus to create the intended modified allele. To enrich for ES cells that have incorporated the targeting vector into their genomes, the targeting vector typically includes a gene or sequence that encodes a protein that imparts resistance to a drug that would otherwise kill an ES cell. The drug resistance gene is referred to as a selectable marker because in the presence of the drug, ES cells that have incorporated and express the resistance gene will survive, that is, be selected, and form clonal colonies, whereas those that do not express the resistance gene will perish. Such a selectable marker is typically present in a selection cassette, which typically includes nucleic acid sequences that will allow for expression of the selectable marker. Molecular assays on drug-resistant ES cell colonies identify those rare clones in which homologous recombination between the targeting vector and the target gene results in the intended modified sequence (e.g., the intended modified allele).

After selection of drug-resistant clones, the selection cassette typically serves no further function for the modified allele. Ideally the cassette should be removed, leaving an allele with only the intended genetic modification, because the selection cassette might interfere with the expression a neighboring gene such as a reporter gene, which is often incorporated adjacent to the selectable marker in many knockout alleles, or might interfere with a nearby endogenous gene (see, e.g., Olsen et al. (1996) Know Your Neighbors: Three Phenotypes of the Myogenic bHLH Gene MRF4. Cell 85:1-4; Strathdee et al. (2006) Expression of Transgenes Targeted to the Gt(ROSA)26Sor Locus Is Orientation Dependent, PloS ONE 1(1):e4.). Either event can confound the interpretation of the phenotype of the modified allele. For these reasons selectable markers in knockout alleles are usually flanked by recognition sites for site-specific recombinase enzymes, for example, loxP sites, which are recognized by the Cre recombinase (see, e.g., Dymecki (1999) Site-specific recombination in cells and mice, in Gene Targeting: A Practical Approach, 2d Ed., 37-99). A typical selection cassette comprises a promoter that is active in ES cells linked to the coding sequence of an enzyme, such as neomycin phosphotransferase, hat imparts resistance to a drug, such as G418, followed by a polyadenylation signal, which promotes transcription termination and 3' end formation and polyadenylation of the transcribed mRNA. This entire unit is flanked by recombinase recognition sites oriented to promote deletion of the selection cassette upon the action of the cognate recombinase.

Recombinase-catalyzed removal of the selection cassette from the knockout allele is typically achieved either in the gene-targeted ES cells by transient expression of an introduced plasmid carrying the recombinase gene or by breeding mice derived from the targeted ES cells with mice that carry a transgenic insertion of the recombinase gene. Either method has its drawbacks. Selection cassette excision by transient transfection of ES cells is not 100% efficient. Incomplete excision necessitates isolating multiple subclones that must be screened for loss of the selectable marker, a process that can take one to two months and subject a targeted clone to high levels of recombinase and a second round of electroporation and plating that can adversely affect the targeted clone's ability to transmit the modified allele through the germline. Consequently, the process might require repetition on multiple targeted clones to ensure the successful creation of knockout mice from the cassette-deleted clones.

The alternative approach of removing the selection cassette in mice requires even more effort. To achieve complete removal of the selection cassette from all tissues and organs, mice that carry the knockout allele must be bred to an effective general recombinase deletor strain. But even the best deletor strains are less than 100% efficient at promoting cassette excision of all knockout alleles in all tissues. Therefore, progeny mice must be screened for correct recombinants in which the cassette has been excised. Because mice that appear to have undergone successful cassette excision may still be mosaic (i.e., cassette deletion was not complete in all cell and tissue types), a second round of breeding is required to pass the cassette-excised allele through the germline and ensure the establishment of a mouse line completely devoid of the selectable marker. In addition to about six months for two generations of breeding and the associated housing costs, this process may introduce undesired mixed strain backgrounds through breeding, which can make interpretation of the knockout phenotype difficult.

Accordingly, there remains a need in the art for compositions and methods for excising nucleic acid sequences in genetically modified cells and animals.

SUMMARY

Compositions and methods for excising nucleic acid sequences in genetically modified cells and animals are provided, and, in particular, for excising nucleic acid sequences.

In one aspect, an expression construct is provided, wherein the expression construct comprises a promoter operably linked to a gene encoding a site-specific recombinase (recombinase), wherein the promoter drives transcription of the recombinase in differentiated cells, but does not drive transcription of the recombinase in undifferentiated cells. Undifferentiated cells include ES cells, e.g., mouse ES cells.

In one embodiment, the expression construct further comprises a selection cassette, wherein the selection cassette is disposed between a first recombinase recognition site (RRS) and a second RRS, wherein the recombinase recognizes both the first and the second RRS.

In one embodiment, the first and the second RRS are non-identical. In one embodiment, the first and the second RRS are independently selected from a loxp, lox511, lox2272, lox66, lox71, loxM2, lox5171, FRT, FRT11, FRT71, attp, att, FRT, or Dre site.

In one embodiment, the first and the second RRS are oriented so as to direct a deletion in the presence of the recombinase.

In one embodiment, the selection cassette comprises a gene that confers resistance to a drug.

In one aspect, a method for excising a selectable marker from a genome is provided, comprising the step of allowing a cell to differentiate, wherein the cell comprises a selection cassette, wherein the selection cassette is flanked 5' and 3' by site-specific recombinase recognition sites (RRSs); and wherein the cell further comprises a promoter operably linked to a gene encoding a recombinase that recognizes the RRSs, wherein the promoter drives transcription of the recombinase in differentiated cells at least 10-fold higher than it drives transcription of the recombinase in undifferentiated cells, wherein following expression of the recombinase, the selection cassette is excised.

In one embodiment, the promoter drives transcription in differentiated cells about 20-, 30-, 40-, 50-, or 100-fold higher than it drives transcription in undifferentiated cells. In one embodiment, the promoter does not substantially drive transcription in undifferentiated cells, but drives transcription in differentiated cells.

In one embodiment, expression of the recombinase in a culture of cells maintained under conditions sufficient to inhibit differentiation, occurs in no more than about 0.1, 0.2, 0.3, 0.4, 0.5, 0.6, 0.7, 0.8, or 0.9% of the cells of the culture. In one embodiment, expression occurs in no more than about 1, 2, 3, 4, or 5% of the cells of the culture.

In one embodiment, the promoter is selected from a Prm1 (aka, Prdm1), Blimp1, Gata6, Gata4, Igf2, Lhx2, Lhx5, Pax3. In a specific embodiment, the promoter is the Gata6 or Gata4 promoter. In another specific embodiment, the promoter is a Prm1 promoter. In another specific embodiment, the promoter is a Blimp1 promoter or fragment thereof, e.g., a 1 kb or 2 kb fragment of a Blimp1 promoter.

In one embodiment, the cassette is on a separate nucleic acid molecule than the recombinase gene. In one embodiment, the selection cassette and the recombinase gene are on a single nucleic acid molecule. In a specific embodiment, RSSs flank, 5' and 3', a nucleic acid sequence that includes the selection cassette and the recombinase gene, such that after the recombinase binds the RSSs, the recombinase gene and the selection cassette are simultaneously excised.

In one embodiment, the selection cassette is on a first targeting vector and the recombinase gene is on a second targeting vector, wherein the first and the second targeting vector each comprise mouse targeting arms.

In one embodiment, the selection cassette and the recombinase gene are both on the same targeting vector. In one embodiment, the cassette and the recombinase gene are each positioned between the same two RRSs. In one embodiment, the RRSs are arranged so as to direct a deletion. In one embodiment, the RRSs are non-identical. In one embodiment, the RRSs are each recognized by the same recombinase. In a specific embodiment, the RRSs are non-identical, are recognized by the same recombinase, and are oriented to direct a deletion of the recombinase gene and the cassette. In a specific embodiment, the RRSs are identical and are oriented to direct a deletion of the recombinase gene and the cassette.

In a specific embodiment, the targeting vector comprises, from 5' to 3' with respect to the direction of transcription, a reporter gene; a first RRS; a selectable marker driven by a first promoter; a second promoter selected from a Prm1, Blimp1, Gata6 and Gata4 promoter, wherein the second promoter is operably linked to a sequence encoding a recombinase; and a second RRS; wherein the first and the second RRS are in the same orientation (i.e., in an orientation that, in the presence of the recombinase, directs deletion of sequences flanked by the RRSs).

In one embodiment, allowing the cell to differentiate comprises removing or substantially removing from the presence of the cell a factor that inhibits differentiation. In a specific embodiment, the factor is removed by washing the cell or by dilution of the cell in a medium that lacks the factor that inhibits differentiation. In one embodiment, allowing the cell to differentiate comprises exposing the cell to a differentiation factor at a concentration that promotes differentiation of the cell.

In one aspect, a targeting vector is provided, wherein the targeting vector comprises (a) a selection cassette; and, (b) a promoter operably linked to a gene encoding a recombinase; wherein the cassette is flanked 5' and 3' by RRSs recognized by the recombinase, wherein the promoter drives transcription of the recombinase in differentiated cells, but not in undifferentiated cells.

In one embodiment the targeting vector further comprises flanking targeting arms, each of which are mouse or rat targeting arms.

In one embodiment, the targeting vector further comprises a reporter gene. In one embodiment, the reporter gene is selected from the following genes: luciferase, lacZ, green fluorescent protein (GFP), eGFP, CFP, YFP, eYFP, BFP, eBFP, DsRed, and MmGFP. In a specific embodiment, the reporter gene is a lacZ gene.

In one embodiment, expression of a selectable marker of the selection cassette (e.g., neo$^r$) is driven by a promoter selected from a UbC promoter, an hCMV promoter, an mCMV promoter, a CAGGS promoter, an EF1 promoter, a Pgk1 promoter, a beta-actin promoter, and a ROSA26 promoter.

In one embodiment, the gene encoding the recombinase is driven by a promoter selected from the group consisting of the following promoters: a Prm1, Blimp1, Blimp1 (1 kb fragment), Blimp1 (2 kb fragment), Gata6, Gata4, Igf2, Lhx2, Lhx5, and Pax3. In a specific embodiment, the promoter is the Gata6 or Gata4 promoter. In another specific embodiment, the promoter is a Prm1 promoter. In another specific embodiment, the promoter is a Blimp1 promoter or fragment thereof, e.g., a 1 kb fragment or 2 kb fragment as described herein.

In one embodiment, the recombinase is selected from the group consisting of the following recombinases: Cre, Flp (e.g., Flpe, Flpo), and Dre.

In one embodiment, the RRSs are independently selected from a loxp, lox511, lox2272, lox66, lox71, loxM2, lox5171, FRT, FRT11, FRT71, attp, att, FRT, or Dre site.

In one embodiment, the selection cassette comprises a selectable marker from the group consisting of the following genes: neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and Herpes simplex virus thymidine kinase (HSV-tk). In a specific embodiment, the selection cassette comprises a neo$^r$ gene driven by a UbC promoter.

In one embodiment, the targeting vector comprises (a) a selection cassette flanked 5' and 3' by a loxp site; and, (b) a Prm1, Blimp1, Gata6, Gata4, Igf2, Lhx2, Lhx5, or Pax3 promoter operably linked to a gene encoding a Cre recombinase, wherein the Gata6, Gata4, Igf2, Lhx2, Lhx5, or Pax3 promoter drives transcription of the Cre recombinase in differentiated cells, but does not drive transcription, or does not substantially drive transcription, in undifferentiated cells.

In one embodiment, the targeting vector comprises, from 5' to 3' with respect to the direction of transcription of the targeted gene: (a) a 5' targeting arm; (b) a reporter gene; (c) a first RRS; (d) a selection cassette; (e) a promoter operably linked to a nucleic acid sequence encoding a recombinase; (f) a second RRS; and, (g) a 3' targeting arm; wherein the promoter drives transcription of the recombinase gene in differentiated cells, and does not drive transcription of the recombinase gene in undifferentiated cells or does not substantially drive transcription of the recombinase in undifferentiated cells.

In one aspect, a method for excising a nucleic acid sequence in a genetically modified non-human cell is provided, comprising a step of allowing a cell to differentiate, wherein the cell comprises a selection cassette flanked 5' and 3' by RRSs and further comprises a promoter operably linked to a gene encoding a recombinase that recognizes the RRSs, further comprising a 3'-UTR of the recombinase gene, wherein the 3'-UTR of the recombinase gene comprises a sequence recognized by an miRNA that is active in an undifferentiated cell but is not active in a differentiated cell, wherein following differentiation, the recombinase gene is transcribed and expressed such that the selection cassette is excised.

In one embodiment, the miRNA is present in the undifferentiated cell at a level that inhibits or substantially inhibits expression or the recombinase gene; wherein the miRNA is absent in a differentiated cell or is present in a differentiated cell at a level that does not inhibit, or does not substantially inhibit, expression of the recombinase gene.

In one aspect, a targeting vector is provided, wherein the targeting vector comprises a nucleic acid sequence encoding a recombinase followed by a 3'-UTR, wherein the 3'-UTR comprises an miRNA recognition site, wherein the miRNA recognition site is recognized by an miRNA that is active in undifferentiated cells and is not active in differentiated cells.

In one aspect, a targeting vector is provided, wherein the targeting vector comprises, from 5' to 3' with respect to the direction of transcription of the targeted gene: (a) a 5' targeting arm; (b) a reporter gene; (c) a first RRS; (d) a nucleic acid sequence encoding a selectable marker operably linked to a first promoter that drives expression of the marker; (e) a recombinase gene operably linked to a second promoter; (g) a 3'-UTR comprising an miRNA recognition site, wherein the miRNA recognition site is recognized by an miRNA that is active in undifferentiated cells and is not active in differentiated cells; (h) a second RRS; and, (i) a 3' targeting arm.

In one embodiment the miRNA recognition site recognizes an miRNA of the miR-290 cluster. In one embodiment, the miR-290 cluster member is miR-292-3p, 290-3p, 291a-3p, 291b-3p, 294, or 295; in a specific embodiment, the miRNA recognition site comprises a seed sequence of one or more of the aforementioned miR-290 cluster members. In a specific embodiment, the miRNA recognition site recognizes an miRNA that comprises the seed sequence of miR-292-3p or miR-294.

In one embodiment, the miRNA recognition site recognizes an miRNA of the miR-302 cluster (miR-302a, 302b, 302c, 302d, and 367). In one embodiment, the miR-302 cluster member is miR-302a, 302b, 302c, or 302d; in a specific embodiment, the miRNA recognition site comprises a seed sequence of one or more of the aforementioned miR-302 cluster members.

In one embodiment, the miRNA recognition site recognizes an miRNA of the miR-17 family (miR-17, miR-18a, miR-18b, miR-20a). In one embodiment, the miR-17 family member is miR-17, miR-18a, miR-18b, miR-20a; in a specific embodiment, the miRNA recognition site comprises a seed sequence of one or more of miR-17, miR-18a, miR-18b, or miR-20a.

In one embodiment, the miRNA recognition site recognizes an miRNA of the miR-17-92 family (including miR-106 and miR-93). In one embodiment, the family member is miR-106a, miR-18a, miR-18b, miR-93, or miR-20a; in a specific embodiment, the miRNA recognition site comprises a seed sequence of one or more of miR-106a, miR-18a, miR-18b, miR-93, or miR-20a.

In one embodiment, the miRNA recognition site recognizes an miRNA whose seed sequence (nucleotides 2 to 8 from the 5' end) is identical or has 6 out of 7 nucleotides of the seed sequence of an miRNA selected from miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93. In one embodiment, the miRNA recognition site further comprises a sequence outside of the seed recognition site, wherein the sequence outside of the seed recognition site is substantially complementary to the non-seed sequence of a miRNA selected from miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93. In a specific embodiment, the miRNA recognition site comprises a sequence outside of the seed recognition site has a complementarity of about 80%, 85%, 90%, or 95% with a non-seed sequence of a miRNA selected from miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93. In a specific embodiment, the non-seed sequence of the miRNA recognition site is perfectly complementary to a non-seed sequence of an miRNA selected from miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93.

In one embodiment, the reporter gene is selected from luciferase, lacZ, green fluorescent protein (GFP), eGFP, CFP, YFP, eYFP, BFP, eBFP, DsRed, and MmGFP. In a specific embodiment, the reporter gene is a lacZ gene. The reporter gene may be any suitable reporter gene.

In one embodiment, the selection cassette comprises a gene selected from the group consisting of the following genes: neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), Herpes simplex virus thymidine kinase (HSV-tk). In a specific embodiment, the selection cassette comprises a neo$^r$ gene driven by a UbC promoter.

In one embodiment, the recombinase is selected from the group consisting of the following site-specific recombinases (SSRs): Cre, Flp, and Dre.

In one embodiment, the first and the second RRSs are independently selected from a loxp, lox511, lox2272, lox66, lox71, loxM2, lox5171, FRT, FRT11, FRT71, attp, att, FRT, or Dre site.

In one aspect, a method for excising a selection cassette in a genetically modified mouse cell or mouse is provided, comprising employing a targeting vector comprising a selection cassette and a recombinase gene operably linked to a 3'-UTR comprising an miRNA as described herein to target a sequence in a donor mouse ES cell, growing the donor mouse ES cell under selection conditions, introducing the donor mouse ES cell into a mouse host embryo to form a genetically modified embryo comprising the donor ES cell, introducing the genetically modified embryo into a mouse that is capable of gestating the embryo, maintaining the mouse under conditions that allow for gestation, wherein upon differentiation the selection cassette is excised.

In one aspect, a method is provided for maintaining non-human cells in culture in an undifferentiated state, comprising genetically modifying an undifferentiated cell with a targeting vector as disclosed herein that comprises a selectable marker flanked on each side by site-specific recombinase recognition sites and a recombinase gene under control of a promoter as disclosed herein and/or comprising a 3'-UTR having an miRNA recognition sequence as described herein, and growing the undifferentiated cell under selective conditions, wherein the recombinase gene is transcribed and the selectable marker is excised in the event of differentiation of the cell.

In one embodiment, the non-human cell is selected from a pluripotent cell, a totipotent cell, and an induced pluripotent cell. In one embodiment, the non-human cell is an ES cell. In specific embodiments, the non-human cell is selected from a mouse ES cell and a rat ES cell.

In one aspect, a method is provided for maintaining a culture enriched with undifferentiated cells, comprising growing the cells in the presence of a selection agent, wherein the cells comprise a selection cassette that allows the cells to grow in the presence of the selection agent, wherein the selection cassette is flanked 5' and 3' by a RSS that is recognized by a recombinase, wherein the cells comprise a gene encoding the recombinase, wherein the gene encoding the recombinase (a) is operably linked to a promoter selected from the group consisting of a Blimp1 promoter or a Prm1 promoter; or, (b) comprises in its 3'-UTR a miRNA recognition sequence that is a target for an miRNA selected from the group consisting of miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, and miR-93; or, (c) is operably linked to a promoter as in (a) and also comprises an miRNA recognition sequence as in (b).

In one aspect, a cell is provided that comprises a recombinase gene that is (a) operably linked to a promoter that is inactive or substantially inactive in non-germ cells but active in germ cells, and/or (b) operably linked to a miRNA recognition sequence as described herein; wherein the cell comprises a selection cassette flanked upstream and downstream with RRSs recognized by the recombinase and that are oriented to direct a deletion. In one embodiment, the cell is selected from an induced pluripotent cell, a pluripotent cell, and a totipotent cell. In one embodiment, the cell is a mouse cell. In a specific embodiment, the mouse cell is a mouse ES cell.

In one embodiment, the germ cell is a sperm lineage cell. In one embodiment, the promoter that is inactive or substantially inactive in non-germ cells but active in a germ cell is a Prm1 promoter.

In one aspect, a kit is provided, comprising a nucleic acid construct that comprises a recombinase gene operably linked to a miRNA recognition sequence as described herein, and a selection cassette flanked 5' and 3' by RSSs that are recognized by a recombinase expressed by the recombinase gene.

In one aspect, a kit is provided, comprising a nucleic acid construct that comprises a recombinase gene operably linked to a promoter that is does not drive transcription of the recombinase in undifferentiated cells but that drives transcription of the recombinase in differentiated cells, and a selection cassette flanked 5' and 3' by RSSs that are recognized by a recombinase expressed from the recombinase gene.

Other embodiments will become apparent from a review of the ensuing detailed description.

BRIEF DESCRIPTION OF THE FIGURES

FIG. 2 illustrates alignments of miRNAs of the miR-290 cluster and related miRNAs, including those abundant in ES cells. SEQ ID NOs are: SEQ ID NO:23 (292-5p); SEQ ID NO:46 (290-5p); SEQ ID NO:21 (291a-5p); SEQ ID NO:47 (291b-5p); SEQ ID NO:48 (293*); SEQ ID NO:49 (294*); SEQ ID NO:50 (295*); SEQ ID NO:51 (302a*); SEQ ID NO:52 (302b*); SEQ ID NO:53 (302c*); SEQ ID NO:54 (17*); SEQ ID NO:55 (18*); SEQ ID NO:56 (20a*); SEQ ID NO:26 (292-3p); SEQ ID NO:22 (290-3p); SEQ ID NO:24 (291a-3p); SEQ ID NO:25 (291b-3p); SEQ ID NO:27 (293); SEQ ID NO:28 (294); SEQ ID NO:29 (295); SEQ ID NO:30 (302a); SEQ ID NO:31 (302b); SEQ ID NO:32 (302c); SEQ ID NO:33 (302d); SEQ ID NO:34 (367); SEQ ID NO:4 (17); SEQ ID NO:5 (18a); and SEQ ID NO:8 (20a).

FIG. 3 illustrates an miRNA recognition sequence according to an embodiment of the invention, having four tandem copies of an miR-292-3p recognition sequence for insertion in a 3'-UTR of an NL-Crei gene in a targeting vector. The SEQ ID NOs are: SEQ ID NO:57 (S1); SEQ ID NO:58 (AS1); SEQ ID NO:59 (S2); and SEQ ID NO:60 (AS2).

DETAILED DESCRIPTION

Figure 1:
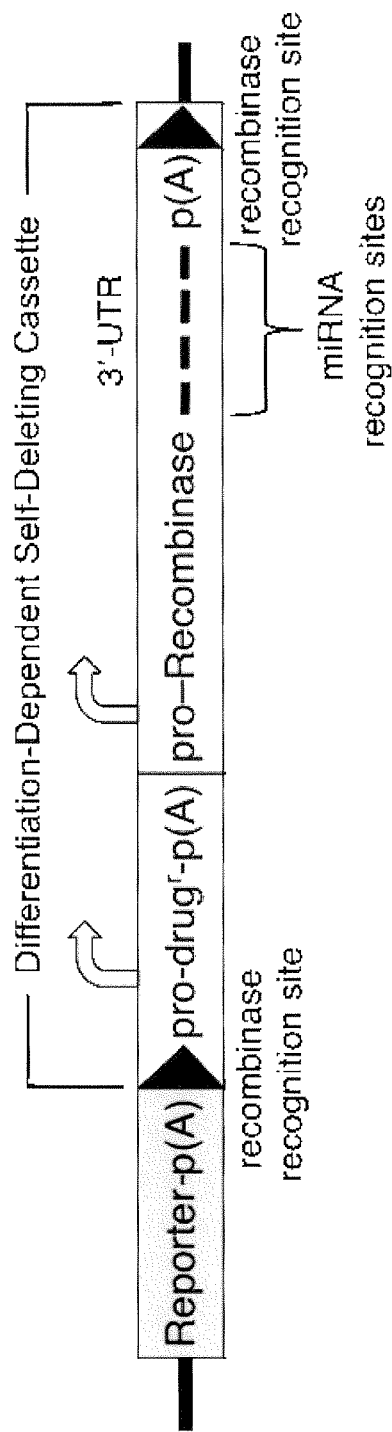
FIG. 1 illustrates a targeting vector according to an embodiment of the invention that comprises an miRNA recognition site in the 3'-UTR of a recombinase gene.

The invention is not limited to particular methods, and experimental conditions described, as such methods and conditions may vary. The terminology used herein is for the purpose of describing particular embodiments only, and is not intended to be limiting, since the scope of the present invention will be limited only by the claims.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, particular methods and materials are now described. All publications mentioned herein are incorporated herein by reference in their entirety.

Methods and compositions are provided for modifying or removing nucleic acid sequences in a differentiation-dependent manner. The methods and compositions include promoters or regulatory elements that induce modification (e.g., inversion) or removal (e.g., excision) of a nucleic acid sequence only when a cell undergoes differentiation or begins a differentiation process. The methods and compositions also include those that employ sequences recognized by miRNAs that are produced and/or function in undifferentiated cells but cease to be produced or cease to function in differentiated cells. They also include promoters that drive transcription effectively in differentiated cells, but not effectively in undifferentiated cells.

Differentiation-Dependent Regulation of Expression: Promoters and RNAs

An ideal solution to the problem of selectable marker removal from genetically modified animals (e.g., knockout mice) would retain the selection cassette in ES cells to enable selection of clones that have incorporated the targeting vector but promote automatic excision (or modification, e.g., inversion) of the cassette with essentially 100% efficiency in all cells and tissues of the developing embryo and mouse without the need for additional treatments or manipulations of targeted ES cells or for breeding of mice. Such an ideal solution depends upon the recombinase that recognizes the recombination sites flanking the selection cassette being inactive, or substantially inactive, in undifferentiated ES cells and then becoming active once the ES cells are incorporated into a developing embryo and begin to differentiate.

One way of achieving differentiation-dependent regulation of the recombinase is to drive the transcription of recombinase mRNA with a promoter that is off in ES cells but comes on once the ES cells begin to differentiate (e.g., into the cell and tissue types of a developing embryo) or, e.g., that is on in a germ cell such that progeny that develop from the germ cell have expressed the recombinase at a very early stage in development. In this way, a selection cassette flanked on each side by recombinase recognition sites is excised only upon differentiation (or development). For complete excision of the selection cassette, the promoter driving recombinase expression would, ideally, remain active in all the cells and tissues of the embryo and mouse. However, certain promoters, e.g., those active in germ cells, might also be useful because if the promoter is active in a germ cell of an F0 animal, breeding that animal will result in excision of the cassette in all cells and tissues of that animal's progeny.

Embodiments are provided for promoters that are inactive in ES cells that have not undergone differentiation, but that are active either during differentiation or when the ES cells begin to differentiate (or, e.g., in germ cells or in germ lineage cells, e.g., in sperm lineage cells). A recombinase gene operably linked to such a promoter will be transcribed, or substantially transcribed, when an ES cell begins to differentiate (or, e.g., when a cell differentiates into a germ lineage cell, e.g., a sperm lineage cell). If a selection cassette is flanked by recombinase recognition sites that direct a deletion, then expression of the recombinase will cause the differentiating cell to lose the selection cassette and, if the cells are maintained under selective conditions, the cells will not survive selection. This affords methods and compositions for maintaining only undifferentiated ES cells in culture, for maintaining an ES cell culture enriched with respect to undifferentiated cells, and for automatic excision of a selection cassette upon differentiation of the ES cells while, e.g., the ES cells are differentiating as donor cells in a host embryo.

In various embodiments, a suitable promoter is selected from a Prm1, Blimp1, Gata6, Gata4, Igf2, Lhx2, Lhx5, Pax3. In a specific embodiment, the promoter is the Gata6 or Gata4 promoter. In another specific embodiment, the promoter is a Prm1 promoter. In another specific embodiment, the promoter is a Blimp1 promoter or fragment thereof, e.g., a 1 kb or 2 kb fragment of a Blimp1 promoter. A suitable Prm1 promoter is shown in SEQ ID NO:1; a suitable Blimp1 promoter is shown in SEQ ID NO:2 (1 kb promoter) or SEQ ID NO:3 (2 kb promoter).

Differentiation-Dependent Regulation: mirna Recognition Sequences

Another way of achieving differentiation-dependent regulation of the recombinase is to regulate recombinase expression post-transcriptionally by miRNA-mediated mechanisms. Micro RNAs (miRNAs) are small RNAs (approximately 22 nucleotides, nt, in length) that associate with Argonaute proteins and regulate mRNA expression by binding to miRNA recognition sites in the 3'-untranslated region (3'-UTR) of mRNA and promoting inhibition of protein synthesis and destruction of the mRNA (see, e.g., Filipowicz et al. (2008) Mechanisms of post-transcriptional regulation by microRNAs: are the answers in sight? Nature Reviews Genetics 9:102-114).

An miRNA interacts with its natural recognition site by forming a Watson-Crick (W-C) base-paired helix between the miRNA's so-called seed sequence—nucleotides 2 through 8 numbering from the 5' end—and a complementary sequence in the target mRNA's 3'-UTR. The remainder of the miRNA forms an imperfect helix with the target. This type of imperfectly paired complex between the target mRNA and the miRNA bound to an Argonaute protein and other components of the RNA-induced silencing complex (RISC) triggers the events that result in the inhibition of translation of the target mRNA into protein. Another class of natural small RNA known as small interfering RNA (siRNA) is produced by cleavage of long double-stranded RNAs (dsRNAs) into short dsRNAs whose 21 nt (the most frequent length) single strands form a perfect W-C helix over their 5'-terminal 19 nucleotides with the last two 3'-terminal nucleotides left as unpaired overhangs on each end of the helix. Usually, one strand of a double-stranded siRNA gets loaded into an Argonaute-RISC in a manner similar to miRNAs, but unlike miRNAs, siRNA-loaded RISCs form perfect W-C helices with their target mRNAs and promote cleavage rather than translational inhibition. An mRNA cleaved by an siRNA-RISC is usually rapidly degraded by cellular ribonucleases, which usually results in a more severe reduction of the target mRNA and its encoded protein than that induced by a miRNA-RISC. Researchers have taken advantage of this difference to regulate expression of genes exogenously added to cells or animals. See, e.g., Mansfield et al. (2004) MicroRNA-responsive 'sensor' transgenes uncover Hox-like and other developmentally regulated patterns of vertebrate microRNA expression, Nature Genetics 36:1079-1083; Brown et al. (2007) Endogenous microRNA can be broadly exploited to regulate transgene expression according to tissue, lineage and differentiation state, Nature Biotech. 25:1457-1467; Brown et al. (2009) Exploiting and antagonizing microRNA regulation for therapeutic and experimental applications, Nature Reviews Genetics 10:578-585.

All miRNAs mentioned refer to mouse miRNAs, i.e., mmu-miRs.

Differentiation-Dependent miRNA Regulation of an Excising Protein

Differential expression of endogenous miRNAs can be advantageously used to control expression of exogenously added genes in cells and in non-human animals. As discussed above, miRNAs can be potent inhibitors of translation. Where an miRNA has an expression profile that results in inhibition of its target under one set of conditions, but not under another, the difference in expression can be exploited to express a gene under one but not the other set of conditions. Thus, if an endogenous miRNA can be found that is expressed in undifferentiated cells but not in differentiated cells, the expression of a gene controlled by that endogenous miRNA can be modulated by placing a recognition sequence (or target sequence) for the endogenous miRNA in the gene. miRNA expression is expected to modulate expression of the target gene even where the target gene is an exogenous (or foreign) gene so long as the exogenous gene contains, or is operably linked to, an appropriate miRNA recognition sequence. In this way foreign genes, such as those introduced into a cell or a non-human animal by a targeting vector, can be placed under the control of an endogenous miRNA. miRNAs that are expressed only at a certain period in development can be used to silence exogenous genes during that developmental period. Thus, an miRNA that is expressed only in undifferentiated cells but not in differentiated cells can be exploited to silence expression of an exogenous gene in an undifferentiated cell but not following the cell's differentiation, by placing a recognition sequence recognized by the miRNA in operable linkage, e.g., in a 3'-UTR, of the exogenous gene to be silenced.

One advantageous application of placing an miRNA recognition sequence in a 3'-UTR that is a target of a developmentally-regulated miRNA is that nucleic acid sequences in a cell or non-human animal of interest can be modified or excised by a site-specific recombinase in a developmentally-dependent manner. In this application, the sequence desired to be modified or excised is flanked on each side by RRSs, and a recombinase gene is employed that has a 3'-UTR having a target sequence for an miRNA that is expressed in a developmentally-dependent manner. Modification or excision may occur by the option of how the RRSs are oriented. The miRNA recognition sequence is selected by determining at which developmental stage the recombinase gene is to be activated, and selecting the recognition sequence to bind an endogenous miRNA that is expressed at the selected developmental stage. For cases of selection cassette excision discussed herein concerning ES cells, miRNA recognition sequence selection is based on miRNAs that are expressed in undifferentiated cells, but are not expressed in differentiated cells.

Thus, the 3'-UTR of an mRNA of a recombinase is selected so that it contains one or more (e.g., one to four) miRNA recognition sites that comprise perfect (or, in some embodiments, near-perfect) Watson-Crick complements of endogenous natural miRNAs such that use of the sequence in the 3'-UTR of the recombinase produces an siRNA-like RNA interference (RNAi) that results in the reduction of both the targeted recombinase mRNA and its encoded recombinase in cells that express the cognate miRNA.

In various embodiments, the miRNA recognition sites comprise perfect or near-perfect Watson-Crick complements of endogenous natural miRNA seed sequences, or sufficiently recognize natural miRNA seed sequences such that the natural miRNA can bind the target and thus promote inhibition of expression of the gene bearing the target. In various embodiments, the miRNA recognition sequences are present in one, two, three, four, five, or six or more tandem copies in the 3'-UTR. In various embodiments, the miRNA recognition sequences are specific for a single miRNA, in other embodiments, the miRNA recognition sequences bind two or more miRNAs. In various embodiments, the miRNA recognition sequences are identical and designed to bind two or more members of the same miRNA family, e.g., the miRNA recognition sequence is a consensus sequence of two or more miRNA target sequences. In various embodiments, the miRNA recognition sequences are two or more different recognition sequences that bind miRNAs in the same family (e.g., the miR 292-3p family).

miRNAs that are expressed in undifferentiated cells but not in differentiated cells fall into different miRNA families, or clusters. miRNAs that are abundant in ES cells include, e.g., clusters 290-295, 17-92, chr2, chr12, 21, and 15b/6. See, e.g., Calabrese et al. (2007) RNA sequence analysis defines Dicer's role in mouse embryonic stem cells, Proc. Natl. Acad. Sci. USA 104(46):18097-18102; Houbaviy et al. (2003) Developmental Cell 5:351-358, and Landgraf et al. (2007) Cell 129:1401-1414. Quantification of miRNA in mouse ES cells by sequencing of small RNAs revealed that the ten most abundant miRNAs are miR-291a-3p, miR-294, miR-292-5p, miR 295, miR-290, miR 293, miR-292-3p, miR-291a-5p, miR-130a, and miR-96. See, Marson et al. (2008) Cell 134: 521-533, Supplemental FIG. 9. By at least one report based on miRNA quantification by small RNA sequencing, the miR-290-295 clusters miRNAs constitute about 70% of transcribed miRNAs in ES cells. See, Marson et al. (2008), cited above.

As illustrated herein, the ten most abundant miRNAs present in two specific mouse ES cell lines was also determined. Mouse ES cell line VGB6 was isolated at Regeneron Pharmaceuticals, Inc. from a C57BL/6NTac mouse strain (Taconic). Mouse ES cell line VGF1, also isolated at Regeneron Pharmaceuticals, Inc., was isolated from a hybrid 129/B6 F1 mouse strain. The ten most abundant miRNAs were identified by microarray analysis and found to be miR-292-3p, miR-295, miR-294, miR-291a-3p, miR293, miR-720, miR-1224, miR-19b, miR92a, and miR-130a. The top 20 most abundant miRNAs also included, from 11$^{th}$ to 20$^{th}$ most abundant, miR-20b, miR-96, miR-20a, miR-21, miR-142-3p, miR-709, miR-466e-3p, and miR-183.

For the case of VGB6 cells, quantitative PCR revealed that the 20 most abundant miRNAs in those cells are, in order, miR-296-3p, miR-434-5p, miR-494, miR-718, miR-181c, miR-709, miR-699, miR-690, miR-1224, miR-720, miR-370, miR-294, miR-135a*, miR-1900, miR-295, miR-293, miR-706, miR-212, and miR-712.

FIG. 2 shows an alignment of miR290 cluster and related miRNAs. The top panel of FIG. 2 shows miRNAs similar to miR-292-5p (numbered, for the purposes of the alignment, 1-25), whereas the bottom panel shows miRNAs similar to miR-292-3p. Boxed areas indicate nucleotide identity. Based on the sequence similarity shown in the alignments and the functional results described herein, a 3'-UTR of a recombinase gene can contain an miRNA recognition sequence complementary to a miRNA sequence drawn from the miR-292-3p family and related miRNAs shown. The miRNA recognition sequence of the 3'-UTR, in one embodiment, binds an miR-292-3p family member. The miRNA recognition sequence of the 3'-UTR, in one embodiment, binds an miR-292-3p family member that comprises an identical Watson-Crick match in its seed sequence to the miRNA recognition sequence. In another embodiment, the miRNA recognition sequence binds an miR-292-3p family member and has about 85%, about 90%, about 95%, 96%, 97%, 98%, or 99% identity to a sequence of FIG. 2.

The alignment of FIG. 2 showing similarity among 292-3p family members reveals a near-identical seed sequence of 5'-AAGUGCC-3' located at bases 2-8 from the 5' end of the miRNAs of the 292-3p family. This presumably helps members of the 292-3p family bind mRNAs that contain the Watson-Crick complement of 5'-AAGUGCC-3' in their 3'-UTRs. The remainder of the miRNA molecule can form base pairs with the target, but complementarity is not typically perfect for animal miRNAs and their targets.

In one embodiment, the miRNA recognition sequence operably linked to the recombinase gene comprises a seed sequence that comprises a sequence that is identical to 5'-AAGUGCC-3'. In one embodiment, the miRNA recognition sequence operably linked to the recombinase gene comprises a seed sequence that is identical to 5'-AAGUGCC-3' except for a single nucleic acid substitution. In a specific embodiment, the second nucleotide of the seed sequence is a G or an A. In a specific embodiment, the third nucleotide of the seed sequence is a G or a U. In a specific embodiment, the final position of the seed sequence is a C. In a specific embodiment, the final position of the seed sequence is a U. In a specific embodiment, the final position of the seed sequence is an A.

In one embodiment, the miRNA recognition sequence operably linked to the recombinase gene comprises a seed sequence that is perfectly complementary to a seed sequence of an miRNA expressed in an ES cell but not expressed in a differentiated cell, the miRNA is one of the ten most abundant miRNAs expressed in the ES cell in an undifferentiated state, and the miRNA recognition sequence further comprises 14-18 further nucleotides that are about 85%, 90%, 95%, 96%, 97%, 98%, or 99% identical to an miRNA naturally expressed in the undifferentiated ES cell, and wherein the presence of the miRNA recognition sequence in the 3'-UTR of the recombinase gene results in a decrease of expression of at least 50% as compared with a recombinase gene with a 3'-UTR that lacks the miRNA recognition sequence. In a specific embodiment, the decrease in expression of the recombinase is at least 60%, at least 70%, at least 80%, at least 90%, or at least 95%.

In one embodiment, the miRNA recognition sequence comprises a seed sequence of an miRNA selected from miR-292-3p and miR-294. In a specific embodiment, the miRNA recognition sequence further comprises a non-seed sequence that is at least 90% identical with a non-seed sequence of an miRNA selected from the group consisting of miR-292-3p and miR-294. In a specific embodiment, the miRNA recognition sequence further comprises a non-seed sequence that is at least 95% identical with a non-seed sequence of an miRNA selected from the group consisting of miR-292-3p and miR-294.

In one embodiment, the miRNA recognition sequence operably linked to the recombinase gene is recognized by an miRNA selected from miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, and miR-93.

In one embodiment, the miRNA recognition sequence binds miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93, and is one of the 20 most abundant miRs specifically expressed in the target cell. In one embodiment, the miRNA is one of the 10 most abundant miRNAs expressed in the target cell. In one embodiment, the miRNA is one of the five most abundant miRNAs expressed in the target cell. In one embodiment, the target cell is a mouse ES cell and the miRNA is selected from an miR of Table 2. In one embodiment, the miR is selected from the group consisting of miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93, and a combination thereof. In one embodiment, the miRNA recognition sequence comprises a sequence that is complementary to a seed sequence of one of miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93, and the remainder of the miRNA recognition site comprises a non-seed sequence that is about 85%, 90%, 95%, 96%, 97%, 98%, or 99% complementary to a non-seed sequence independently selected from one of miR-292-3p, miR-290-3p, miR-291a-3p, miR-291b-3p, miR-294, miR-295, miR-302a, miR-302b, miR-302c, miR-302d, miR-367, miR-17, miR-18a, miR-18b, miR-20a, miR-106a, or miR-93.

In one embodiment, the miRNA recognition sequence contains a sequence that is a perfect Watson-Crick match to a seed sequence of an miRNA of Table 2, and the remainder of the miRNA recognition sequence (outside of the sequence that perfectly matches the miRNA seed sequence) is 85%, 90%, 95%, 96%, 97%, 98%, or 99% identical to the non-seed sequence of an miRNA of Table 2. In one embodiment, the miRNA is selected from the group consisting of miR-292-3p, miR-295, miR-294, miR-291a-3p, miR-293, miR-720, miR-1224, and a combination thereof. Sequences of miRNAs are provided in Table 1 below.

TABLE 1 mmu-miRNA Sequences

| miR | Sequence | SEQ ID NO |
|---|---|---|
| 17 | CAAAGUGCUUACAGUGCAGGUAG | 4 |
| 18a | UAAGGUGCAUCUAGUGCAGAUA | 5 |
| 18b | UAAGGUGCAUCUAGUGCUGUUAG | 6 |
| 19b | UGUGCAAAUCCAUGCAAAACUGA | 7 |
| 20a | UAAAGUGCUUAUAGUGCAGGUAG | 8 |
| 20b | CAAAGUGCUCAUAGUGCAGGUAG | 9 |
| 21 | UAGCUUAUCAGACUGAUGUUGA | 10 |
| 92a | UAUUGCACUUGUCCCGGCCUG | 11 |
| 93 | CAAAGUGCUGUUCGUGCAGGUAG | 12 |
| 96 | UUUGGCACUAGCACAUUUUUGCU | 13 |
| 106a | CAAAGUGCUUACAGUGCAGGUAG | 14 |
| 130a | CAGUGCAAUGUUAAAGGGCAU | 15 |
| 135a* | UAUAGGGAUUGGAGCCGUGGCG | 16 |
| 142-3p | UGUAGUGUUUCCUACUUUAUGGA | 17 |
| 181c | AACAUUCAACCUGUCGGUGAGU | 18 |
| 183 | GUGAAUUACCGAAGGGCCAUAA | 19 |
| 212 | UAACAGUCUCCAGUCACGGCCA | 20 |
| 291a-5p | CAUCAAAGUGGAGGCCCUCUCU | 21 |
| 290-3p | AAAGUGCCGCCUAGUUUUAAGCCC | 22 |
| 292-5p | ACUCAAACUGGGGGCUCUUUUG | 23 |
| 291a-3p | AAAGUGCUUCCACUUUGUGUGC | 24 |
| 291b-3p | AAAGUGCAUCCAUUUUGUUUGU | 25 |
| 292-3p | AAAGUGCCGCCAGGUUUUGAGUGU | 26 |
| 293 | AGUGCCGCAGAGUUUGUAGUGU | 27 |
| 294 | AAAGUGCUUCCCUUUUGUGUGU | 28 |
| 295 | AAAGUGCUACUACUUUUGAGUCU | 29 |
| 302a | UAAGUGCUUCCAUGUUUUGGUGA | 30 |
| 302b | UAAGUGCUUCCAUGUUUUAGUAG | 31 |
| 302c | AAGUGCUUCCAUGUUUCAGUGG | 32 |
| 302d | UAAGUGCUUCCAUGUUUGAGUGU | 33 |
| 367 | AAUUGCACUUUAGCAAUGGUGA | 34 |
| 370 | GCCUGCUGGGGUGGAACCUGGU | 35 |
| 434-5p | GCUCGACUCAUGGUUUGAACCA | 36 |
| 494 | UGAAACAUACACGGGAAACCUC | 37 |
| 690 | AAAGGCUAGGCUCACAACCAAA | 38 |
| 706 | AGAGAAACCCUGUCUCAAAAAA | 39 |
| 709 | GGAGGCAGAGGCAGGAGGA | 40 |
| 712 | CUCCUUCACCCGGGCGGUACC | 41 |
| 718 | CUUCCGCCCGGCCGGGUGUCG | 42 |
| 720 | AUCUCGCUGGGGCCUCCA | 43 |
| 1224 | GUGAGGACUGGGGAGGUGGAG | 44 |
| 1900 | GGCCGCCCUCUCUGGUCCUUCA | 45 |

Differentiation-Dependent Excision of Selection Cassettes

To create various embodiments of a self-deleting selection cassette whose excision is regulated by miRNA control of recombinase gene expression, a standard selection cassette is modified by insertion of a recombinase gene unit that comprises a promoter, which may or may not be active in ES cells but is active in embryonic stages after the blastocyst, linked to the protein coding sequence of a site-specific recombinase, e.g., Cre, Flp, or Dre, followed by a sequence encoding the 3'-UTR of the recombinase mRNA, into which is inserted a copy of, or multiple copies of, a sequence complementary to one or more miRNAs that are expressed in ES cells but not in any of the cells of the developing embryo or mouse, and terminated with a polyadenylation signal. The modified selection cassette with the inserted miRNA-regulatable recombinase gene unit is flanked by recognition sites for the recombinase whose gene has been inserted. The orientation of the flanking recombinase recognition sites is such that the recombinase will catalyze the deletion of the modified selection cassette, including the recombinase gene. Embodiments are also possible where the selection cassette is on a separate construct, in which case the recombinase works in trans.

In one embodiment, the recombinase gene is a Cre recombinase gene. In one embodiment, the Cre recombinase gene further comprises a nuclear localization signal to facilitate localization of Cre to the nucleus (e.g., the gene is an NL-Cre gene). In one embodiment, the Cre recombinase gene comprises an intron (e.g., the gene is a Crei gene), such that the Cre recombinase is not functional in bacteria. In a specific embodiment, the Cre recombinase gene further comprises a nuclear localization signal and an intron (e.g., NL-Crei).

An example of part of a targeting vector designed to create a knockout allele in which the selectable marker is included within a Differentiation-Dependent Self-Deleting Cassette, or DDSDC, is illustrated in FIG. 1. The rectangle indicates the portion of the targeting vector that inserts at the targeted locus. The thick black lines flanking the rectangle represent parts of the mouse DNA homology arms that promote homologous recombination at the targeted locus. In the example shown, a reporter gene cassette (a common feature of knockout alleles) is shown in which the coding sequence of a reporter protein, such as β-galactosidase or green fluorescent protein, is fused to the targeted gene in such a way as to report the transcriptional activity of the target gene's promoter. The region between the solid triangles (i.e., between the recombinase recognition sites) represents an example of a Differentiation-Dependent Self-Deleting Cassette: the left portion is the selection cassette consisting of gene that encodes a protein that imparts drug resistance (drug$^r$), such as neomycin phosphotransferase, which imparts resistance to the drug G418; the right portion is a gene that encodes a site-specific recombinase, e.g., Cre, Flp, or Dre, containing in its 3'-UTR multiple target sites for one or more ES cell-specific miRNAs. The DDSDC is flanked by the sites (black triangles) recognized by the encoded recombinase, for example, loxP site for the Cre recombinase, FRT sites for the Flp recombinase, or rox sites for the Dre recombinase, oriented such that recombinase action at the sites will promote excision of the DDSDC. The promoters driving expression of the drug$^r$ and recombinase genes are indicated by "pro" with bent arrows above denoting the direction of transcription. In the example shown the drugr and recombinase genes are oriented in the same transcriptional direction, but they could be oriented in either direction. Polyadenylation signals are indicated by "p(A)."

When a modified selection cassette containing the miRNA-regulatable recombinase gene is incorporated into a targeting vector and introduced into mouse ES cells by standard methods of gene targeting known in the art, expression in the ES cells of miRNAs that recognize their target sequence in the 3'-UTR of the recombinase mRNA transcribed from the selection cassette will promote a reduction in recombinase protein synthesis to levels that are too low to substantially excise the selection cassette and, therefore, will permit selection of drug-resistant colonies. As long as the targeted ES cells remain undifferentiated, their endogenous ES-cell-specific miRNAs will control expression of the recombinase and permit drug selection of ES cells that contain the targeted construct. Targeted clones that differentiate away from the ES cell state, however, will lose expression of the ES cell-specific miRNAs, relieving inhibition of recombinase expression, which will result in substantial excision of the selection cassette and loss of drug resistance. Therefore, differentiated clones will be killed (i.e., not survive selection) and would not be used to generate gene-modified mice. Undifferentiated, drug-resistant gene-targeted clones, upon injection into an early mouse embryo (e.g., a premorula, e.g., 8-cell stage embryo, or a blastocyst) will become integrated into the inner cell mass that will ultimately contribute to the developing mouse embryo.

When the injected embryos are transplanted into a surrogate mother and begin to differentiate along a normal developmental path, expression of ES cell-specific miRNAs will wane and the recombinase will be expressed and become active wherever the recombinase gene is transcribed. Driving recombinase expression with a ubiquitously active promoter (e.g., a phosphoglycerate kinase, β-actin, ubiquitin promoter, or other promoter) will ensure that the recombinase will have ample opportunity to excise the selection cassette from all or most cell types during the course of development, resulting in pups born devoid of the selection cassette at the targeted locus. These new-born mice would be ready for phenotypic study without concerns about interference by a selection cassette.

In one embodiment, a method for preparing an ES cell culture that lacks viable differentiated cells is provided, comprising introducing into an ES cell a selection cassette and a recombinase gene, wherein either the selection cassette alone or the recombinase gene and the selection cassette are flanked by RRSs recognized by the recombinase, and the recombinase gene is operably linked to an miRNA target sequence as described herein; growing the ES cell to form an ES cell culture, wherein cells that differentiate in culture lose the selection cassette and expire, thereby forming an ES cell culture that lacks or substantially lacks viable differentiated cells, or comprises a substantially reduced number of viable differentiated cells.

In one embodiment, a method for preparing a population of donor mouse ES cells enriched with respect to undifferentiated ES cells is provided, comprising employing an ES cell as described herein that comprises a selection cassette and a recombinase operably linked to a miRNA recognition sequence as described herein, growing the ES cell to form an ES cell culture, and employing the ES cell culture as a source of donor ES cells for introduction into a mouse host embryo. In one embodiment, the ES cell culture is enriched with respect to undifferentiated ES cells by about 10%, 20%, 30%, 40%, or 50% or that more in comparison to a culture in which ES cells do not comprise the miRNA recognition sequence operably linked to the promoter, and the cells are grown in a medium that requires the selection cassette for survival. In one embodiment, the ES cell culture comprises no more than one viable differentiated cell per 100 cells, no more than one viable differentiated cell per 200 cells, per 300 cells, per 400 cells, per 500 cells, per 1,000 cells, or per 2,000 cells. In a specific embodiment, the ES cell culture comprises no viable differentiated cells.

In one embodiment, a differentiated mouse cell is provided, comprising a recombinase gene operably linked to a miRNA target sequence as described herein, and at least one recombinase recognition site. In one embodiment, the differentiated mouse cell is in a mouse embryo. In one embodiment, the differentiated mouse cell is in a tissue of a mouse. In one embodiment, the differentiated mouse cell further comprises a genetic modification selected from a knock-in, a knockout, a mutated nucleic acid sequence, and an ectopically expressed protein.

In one embodiment, a method for making a genetically modified mouse that lacks a selection cassette is provided, comprising (a) introducing into a mouse host embryo a donor mouse ES cell that comprises (i) a selection cassette flanked 5' and 3' with RSSs oriented to direct a deletion, and a recombinase gene operably linked to a promoter that is inactive in undifferentiated cells but active in differentiated cells; or, (ii) a selection cassette flanked upstream and downstream with RSSs oriented to direct a deletion, and a recombinase gene operably linked to an miRNA target sequence as described herein; (b) introducing the embryo into a suitable host mouse for gestation; and (c) following gestation obtaining a mouse that lacks the selection cassette. In one embodiment, the F0 generation mouse lacks the selection cassette. In one embodiment, the F0 mouse is a chimera wherein less than all cells of the mouse lack the selection cassette, and upon breeding the F0 mouse an F1 generation mouse is obtained that lacks the selection cassette.

In one embodiment, a method for identifying differentiated cells in culture is provided, comprising introducing into an undifferentiated cell (a) a marker cassette that contains a detectable marker gene in antisense orientation, wherein the marker cassette is flanked upstream and downstream with RRSs oriented to direct an inversion; and, (b) a recombinase gene operably linked to (i) a promoter that is inactive in undifferentiated cells but active in differentiated cells, and/or (ii) a miRNA target sequence as described herein; wherein the cell begins to differentiate and the recombinase is expressed and places the detectable marker gene in sense orientation, the detectable marker gene is transcribed, and the cell that begins to differentiate is identified by the expression of the detectable marker. In one embodiment, the detectable marker is a fluorescent protein, and the cell that begins to differentiate is identified by detecting fluorescence from the cell.

EXAMPLES

The following examples are provided to describe to those of ordinary skill in the art a disclosure and description of how to make and use embodiments of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is expressed by degrees Celsius, and pressure is at or near atmospheric.

Example 1 miRNA Abundance in VGB6 and VGF1 ES Cells

Abundance of miRNAs in mouse ES cell lines VGB6 and VGF1 was determined by microarray analysis. Briefly, small RNAs were purified from the ES cells, labeled, and used to probe Agilent miRNA arrays. Abundance readings from array analysis are expressed as hybridization signal intensities.

The twenty most abundant miRNAs are shown based on triplicate readings for VGB6 and for VGF1 in Table 2.

TABLE 2

ES Cell miRNA Microarray Abundance Analysis

| miRNA | miRNA Abundance (avg., n = 3) | |
|---|---|---|
| | VGB6 | VGF1 |
| miR-292-3p | 111769 | 127534 |
| miR-295 | 103566 | 117946 |
| miR-294 | 98411 | 116437 |
| miR-291a-3p | 85478 | 99872 |
| miR-293 | 73418 | 11048 |
| miR-720 | 47419 | 107611 |
| miR-1224 | 41173 | 19402 |
| miR-19b | 28868 | 37820 |
| miR-92a | 27722 | 29698 |
| miR-130a | 22974 | 21864 |
| miR-20b | 18677 | 25450 |
| miR-96 | 16218 | 12988 |
| miR-20a | 15654 | 20744 |
| miR-21 | 15427 | 29023 |
| miR-142-3p | 10369 | 7152 |
| miR-709 | 10078 | 3117 |
| miR-466e-3p | 9645 | 8797 |
| miR-183 | 8714 | 7346 |

The microarray abundance analysis revealed that the top ten abundant miRNAs (ranked by VGB6 abundance) fell largely within the miRNA-290 cluster.

Abundance of miRNAs in VGB6 cells was also determined by quantitative RT-PCR. The qRT-PCR results showed that miRNA-290 family and the miRNA-17-92 family were among the most abundant miRNAs in VGB6 cells.

Example 2

Targeting Vector with miRNA in a Recombinase 3'-UTR

A targeting vector in accordance with an embodiment of the invention is constructed by employing, from 5' to 3' with respect to transcription of the targeted gene, a 5' homology arm, a lacZ reporter gene followed by a polyA sequence, a loxP site, a neo$^r$ gene driven by a UbC promoter, a polyA sequence, a promoter driving expression of a Cre recombinase gene, a 3'-UTR containing four copies of an miR-292-3p target site (see FIG. 3), a polyA sequence, a loxP site, and a 3' homology arm.

Construction of a quadruple miR-292-3p target site by annealing of 4 oligos. To assemble a quadruple miR-292-3p target site, oligodeoxynucleotides S1 and AS1 of FIG. 3 are annealed to produce the hybrid S1:AS1 with Nhe I and Mlu I single-stranded overhangs, oligodeoxynucleotides S2 and AS2 are annealed to produce the hybrid 52:AS2 with Mlu I and Xma I single-stranded overhangs, S1:AS1 and 52:AS2 are annealed through their Mlu I single-stranded overhangs, and the annealed hybrids are inserted into Nhe I and Xma I sites in the 3'-UTR of a recombinase gene. Sequences that are perfect Watson-Crick complements of the mouse miR-292-3p microRNA are labeled "miR-292-3p target" in FIG. 3. Alternatively, a synthetic piece of DNA carrying four miR-292-3p recognition sequences are placed in the 3'-UTR of a Cre recombinase.

The targeting vector containing the miRNA target site of FIG. 3 is employed by homologous recombination of the targeting vector in a mouse ES cell, growing the ES cell under conditions that prevent ES cell differentiating, introducing the ES cell into an early stage embryo (e.g., a premorula) or a blastocyst, and introducing the embryo into a surrogate mother.

Since miR-292-3p is expressed in ES cells, the selection cassette should remain in the ES cell genome during growth and selection of ES cells genetically modified by the targeting vector. To the extent that one or more ES cells bearing the targeting vector would differentiate in culture, those cells would lose the selection cassette and not survive selection.

Once placed into the embryo, the ES cell would divide and populate the embryo. As ES cells within the embryo differentiated, the level of miR-292-3p in the differentiating cell would drop substantially or fall to essentially none. As a result, repression of expression of the Cre recombinase would be relieved, the Cre would express, and the floxed cassette would be excised. Consequently, all or substantially all of the tissues of a mouse born from the surrogate mother would lack the selection cassette.

Example 3

Placement of an miRNA in a 3'-UTR of a Reporter Gene

A commercially available luciferase expression vector was modified by adding a single copy of an exact Watson-Crick complement of an miRNA expressed in ES cells to the 3'-UTR of the luciferase gene. The vector was transiently transfected into the ES cells, and luciferase expression was knocked down as compared to luciferase expression from a vector lacking the miRNA target sequence. This experiment established that placement of an exogenous miRNA into a 3'-UTR of a reporter gene results in an operable unit that can effectively repress gene expression.

Example 4 miRNA Control of Cre Expression in Cells and Mice: Selection

Figure 4:
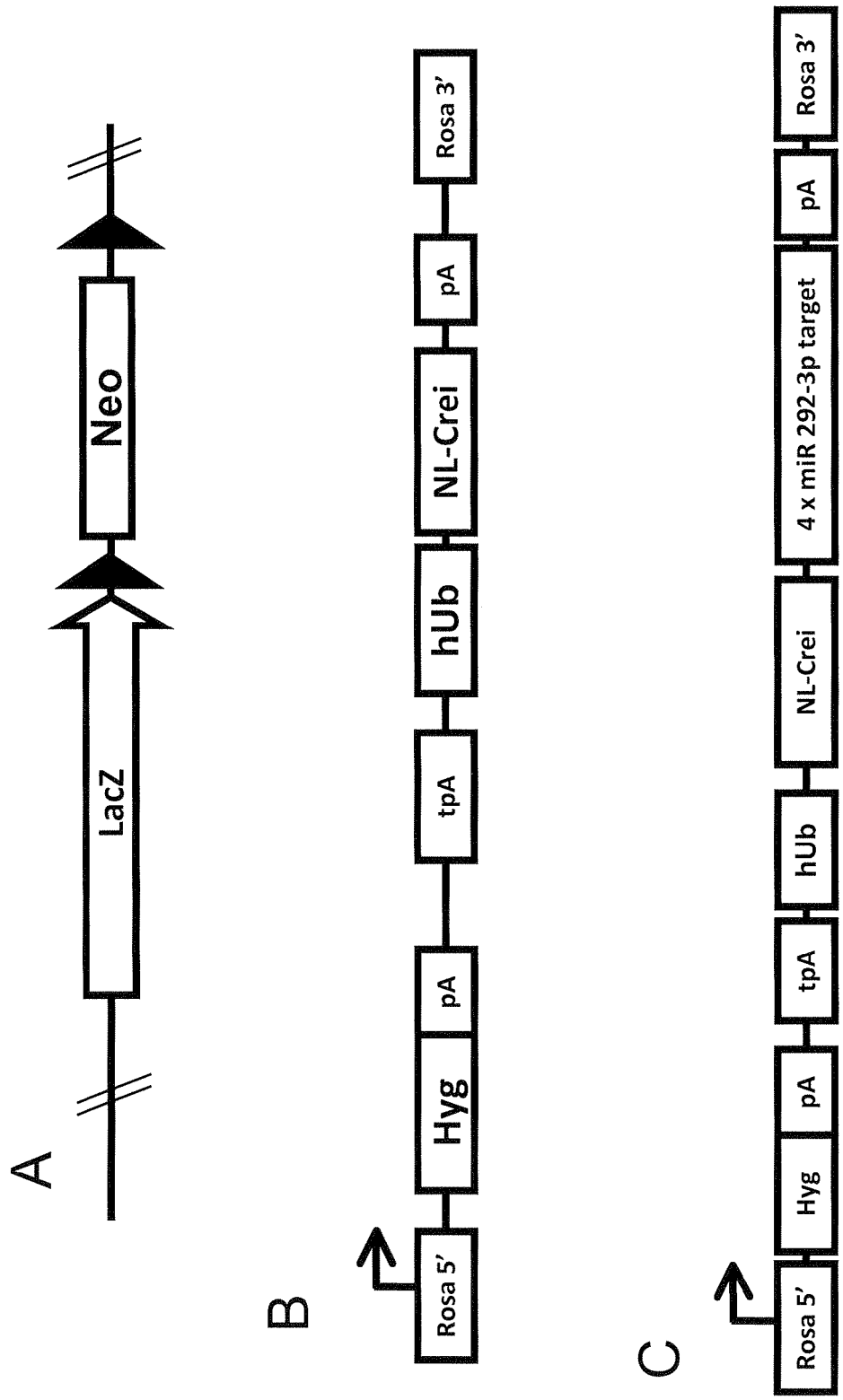
FIG. 4 is a schematic of constructs. Panel A shows a neomycin resistance gene flanked by recombinase recognition sites (RRSs), on a construct having a LacZ gene; Panel B shows a human Ub promoter driving expression of Cre from an NL-Crei gene, on a construct having a hygromycin resistance gene; Panel C shows the construct of Panel B, additionally including a miR recognition sequence 3' with respect to the NL-Crei gene; although not shown, the miR recognition sequence can be present in multiple copies.

Mouse ES cells from a hybrid line (129S6×C57BL6; F1) were electroporated with a first LacZ-containing construct having a floxed neomycin resistance cassette (FIG. 4, Panel A). Cells surviving neomycin selection were then also electroporated with a second construct containing a ROSA26-driven hygromycin resistance cassette and a hUbC-driven NL-Crei gene (FIG. 4, Panel B), or the same second construct but wherein the NL-Crei gene is operably linked to four tandem copies of an miR 292-3p target sequence placed in the NL-Crei 3'-UTR (FIG. 4, Panel C).

The ES cells were genotyped for the presence of the transfected construct and screened for copy number, then introduced into 8-cell stage Swiss Webster embryos using the VELOCIMOUSE® method (see, U.S. Pat. Nos. 7,659,442, 7,576,259, 7,294,754, and Poueymirou et al. (2006) F0 generation mice fully derived from gene-targeted embryonic stem cells allowing immediate phenotypic analyses, Nat. Biotech. 25:91-99; each hereby incorporated by reference). E10.5 embryos fully derived from the transfected hybrid ES cells were analyzed for the presence of the transfected cassettes. Results are shown in Table 3 (Cre 1,2=construct with NL-Crei lacking miRNA in 3'-UTR; Cre-miR 1,2,3=construct with NL-Crei and miR 292-3p target sequence in 3'-UTR). Using these constructs and maintaining the ES cells under conditions selected to retain pluripotency and in the presence of hygromycin or G418 and hygromycin, only those cells that contain the floxed neo cassette but do not express Cre will survive G418 selection. Overall, in all studies, 46% of ES cell clones carrying a floxed selection cassette and a miR-regulated NL-Crei gene exhibited complete deletion of the selection cassette either in embryos or in live-born mice.

Genotyping results for the embryos (whole embryo analyzed) and mice (six tissues analyzed) indicate that regulation of the Cre recombinase by the ES cell-specific miRNAs is relieved upon differentiation and development, as early as day 10.5 of gestation. Live-born mice can be obtained that lack the floxed selection cassette, when multiple tissues are examined.

TABLE 3

Genotyping of E10.5 Embryos and Mice

| Clone | ES Cell Selection | Total Embryos (n) | Neo Deleted Embryos (n) | Neo Deleted Embryos (%) | Total Mice (n) | Neo Deleted Mice (n) | Neo Deleted Mice (%) |
|---|---|---|---|---|---|---|---|
| Parental | — | 4 | 0 | 0 | 2 | 0 | 0 |
| Cre 1 | Hyg | 9 | 9 | 100 | 3 | 3 | 100 |
| Cre 2 | Hyg | 4 | 4 | 100 | 3 | 3 | 100 |
| Cre-miR 1 | Hyg + neo | 6 | 5 | 83.3 | 3 | 3 | 100 |
| Cre-miR 2 | Hyg + neo | 8 | 1 | 12.5 | n.d. | n.d. | n.d. |
| Cre-miR 3 | Hyg + neo | n.d. | n.d. | n.d. | 1 | 1 | 100 |

Genotyping results established that ES cells transfected with a construct comprising NL-Crei operably linked to four copies of a miR 292-3p target sequence (in the NL-Crei gene 3'-UTR) and selected in G418 (i.e., selected for the presence of neo expression) yielded embryos that lacked the neomycin resistance gene (the floxed selection cassette). These results establish that ES donor cells bearing a NL-Crei gene operably linked to a target miRNA sequence for an miRNA expressed in ES cells but not in differentiated cells can be propagated in culture using a suitable selection cassette and, when introduced into a host embryo, the ES cells can perform an automatic deletion of the cassette when they differentiate (and thus no longer express the miRNA that binds to the target miRNA sequence). Therefore, ES cells that bear a selection or marker cassette flanked with recombinase recognition sites, and a recombinase gene operably linked to a miRNA target sequence for a miRNA that is expressed in ES cells but not in differentiated cells, can be maintained in culture such that pluripotency is maintained, and after introduction of the cells into a host embryo and differentiation, the selection or marker cassette is automatically removed.

Figure 6:
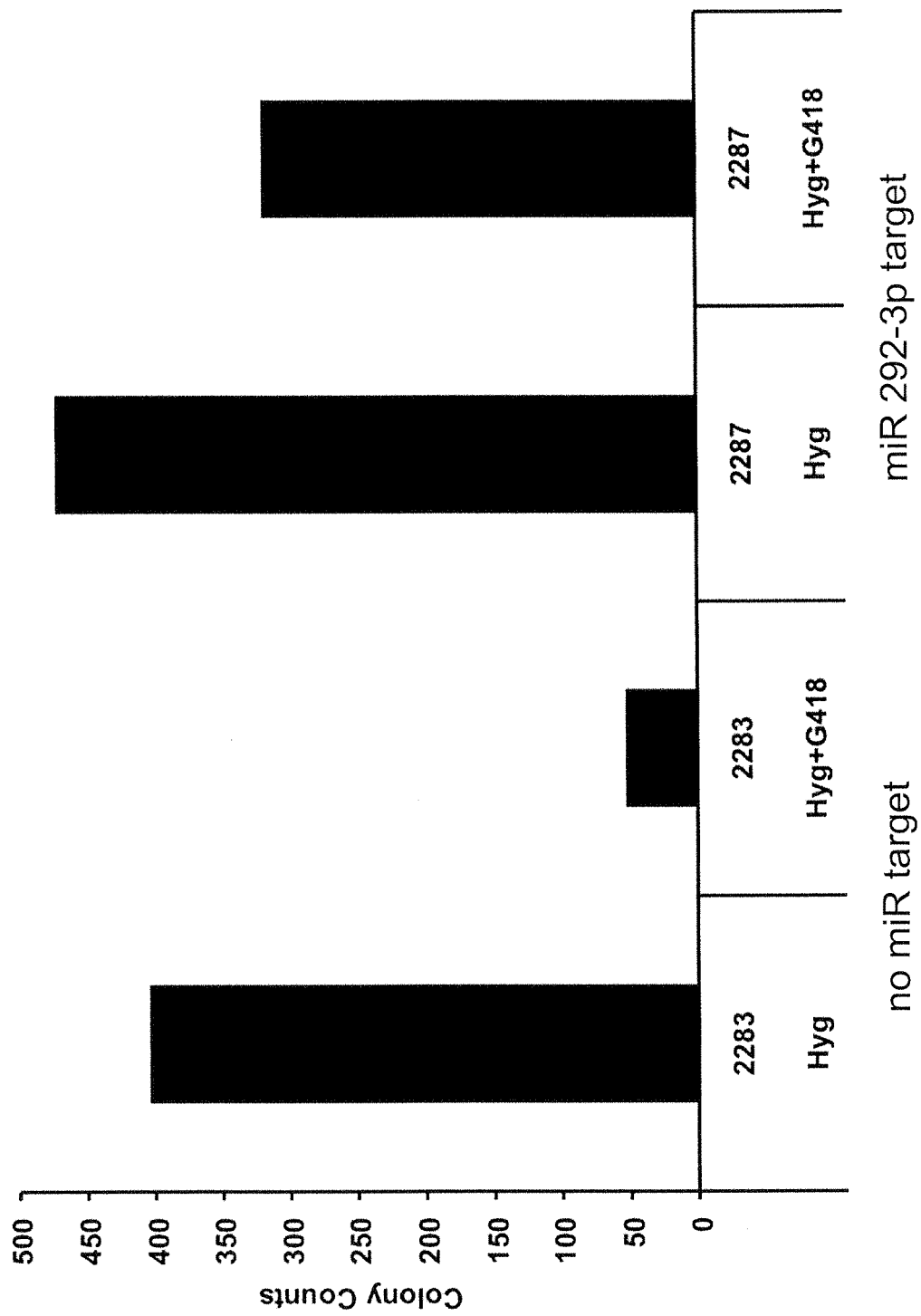
FIG. 6 shows cell count results for mouse ES cells bearing different combinations of constructs of FIG. 4, Panels A, B and C, under different selection conditions.

In in vitro culture studies, cells bearing the NL-Crei gene but lacking the miRNA recognition site in the 3'-UTR (FIG. 4, Panel B) grew well in the presence of hygromycin, but largely expired when G418 was added (FIG. 6, left), indicating that Cre expressed effectively and removed the floxed neo resistance cassette. Cells bearing the NL-Crei gene operably linked to four tandem copies of miR 292-3p target sequence in the NL-Crei 3'-UTR grew well in hygromycin, and also nearly as well in hygromycin and G418 (FIG. 6, right), indicating that the miR recognition sequence inhibited expression of Cre to a significant extent. Essentially the same results were obtained using two different hybrid clones, as well as two clones of an inbred BL/6 ES cell line transfected with the same constructs (data not shown).

In separate experiments, similar cells bearing the constructs described above were grown in the presence of one of either hygromycin, G418, or both, in either the presence or absence of LIF, and/or in the presence or absence of retinoic acid for seven or eight days. Control cells that bore a floxed neo cassette and a constitutive Cre substantially expired in the presence of G418, whereas cells in which the NL-Crei gene was linked to the miR 292-3p target sequences had a substantially lower death rate (as low as about 0-25%, compared with cells lacking the miR target sequence; based on colony counts; data not shown). Cells that bore the NL-Crei gene operably linked to the miR 292-3p target sequences exhibited about a 2- to 3-fold higher death rate—when grown without LIF and in the presence of retinoic acid, hygromycin, and G418—than control cells (based on colony counts; data not shown). Similar results were had with a similar experiment using C57BL/6 ES cells (VGB6 cells).

These results establish that ectopic miRNA recognition sequences can effectively inhibit expression of an ectopically expressed recombinase operably linked to the miRNA recognition sequences, and that this phenomenon can be used to control recombination of recombinase-flanked cassettes in ES cells, including for automatic expression or deletion of the recombinase-flanked cassettes. The results also establish that operably linking an ES cell-specific miRNA recognition sequence to the recombinase gene can assist in maintaining an ES cell culture enriched with respect to undifferentiated ES cells by reducing viability of differentiated cells in a selection medium.

Example 5 miRNA Control of Cre Expression in Cells and Mice: Markers

Figure 7:
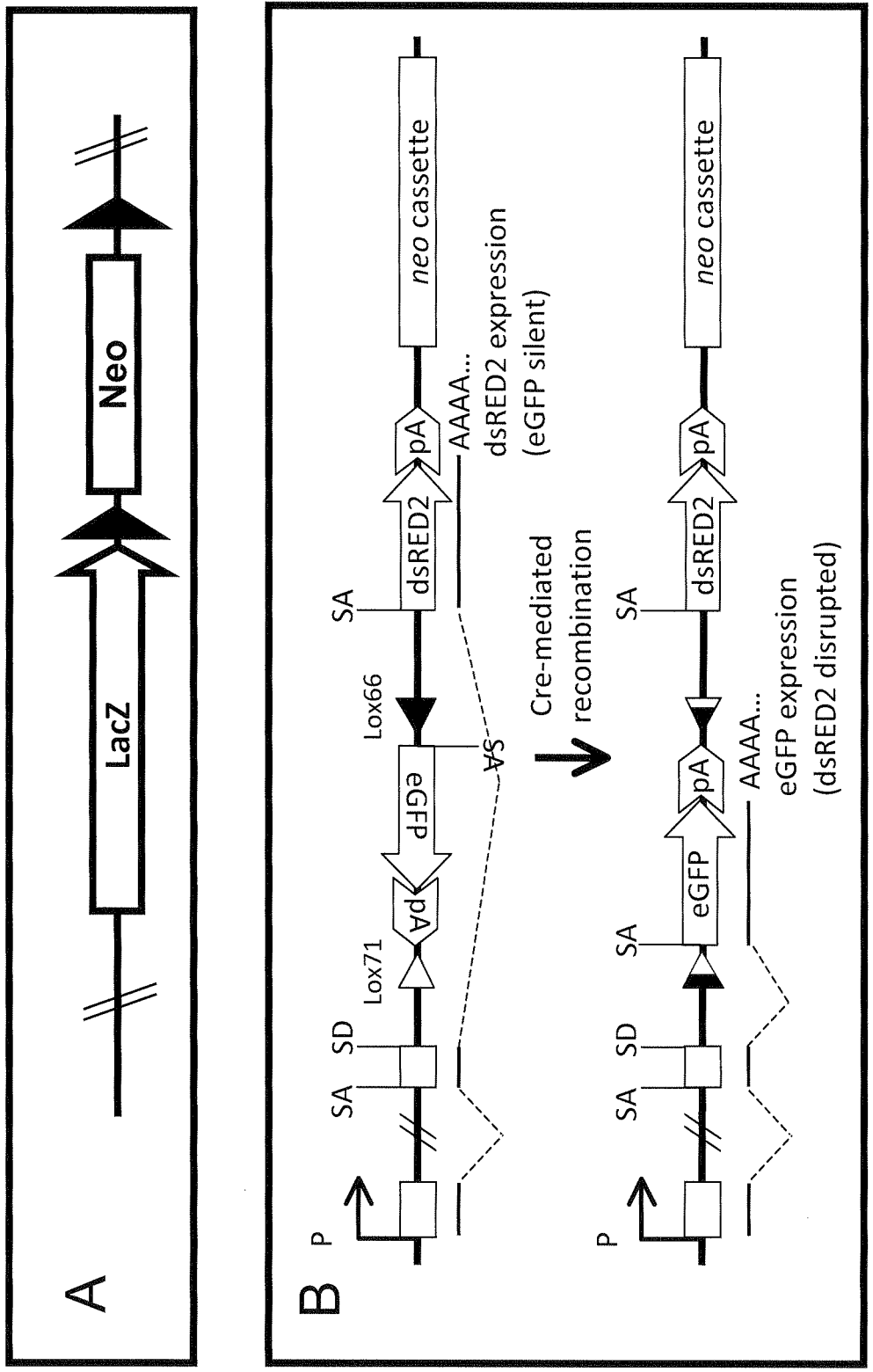
FIG. 7 is a schematic of constructs. Panel A shows a neomycin resistance gene flanked by recombinase recognition sites (RRSs), on a construct having a LacZ gene; Panel B shows a construct having a GFP gene in reverse orientation flanked by incompatible recombinase recognition sites (RRSs), wherein GFP is not expressed, and then recombinase-mediated inversion to place the GFP in orientation for transcription.

Mouse ES cells were transfected as described above with a first construct containing a GFP gene in antisense orientation flanked by non-identical recombinase recognition sites (FIG. 7, Panel B) oriented to direct an inversion, and a second construct containing a ROSA26-driven hygromycin resistance cassette and a hUbC-driven NL-Crei gene (FIG. 4, Panel B), or the same second construct but wherein the NL-Crei gene is operably linked to four tandem copies of an miR 292-3p target sequence placed in the NL-Crei 3'-UTR (FIG. 4, Panel C). Following electroporation, cells were grown in the presence of hygromycin and assayed by FACS for GFP expression.

GFP expression analysis of $2 \times 10^4$ cells each for four separate clones expressing Cre from a hUbC-driven construct in the absence of an miRNA target sequence in the Cre gene 3'-UTR (FIG. 4, Panel B) was conducted on a MOFLO™

(Beckman Coulter) FACS machine. An average of 85.6% of cells exhibited GFP fluorescence. GFP expression analysis of $2\times10^4$ cells each for four separate clones bearing four tandem copies of miR 292-3p in the 3'-UTR of a NL-Crei gene (FIG. 4, Panel C) an average of 46.5% of the cells exhibited GFP fluorescence. Eight other clones similarly tested with or without the miR 292-3p in the NL-Crei 3'-UTR yielded similar results: an average of 91.3% cells expressed GFP in the absence of the miRNA target sequence, whereas an average of only 48.7% of cells expressed GFP in the presence of the miR 292-3p target sequence. Neither culture was inspected for the presence of differentiating cells.

In contrast, clones containing a construct having an NL-Crei gene having four tandem copies of a miR 291a-5p target sequence, or four tandem copies of a miR 1-1 target sequence, in its 3'-UTR showed essentially no difference in GFP expression as measured by FACS as compared with clones containing the same NL-Crei gene but lacking any miR target sequences. These results establish that inhibition of Cre gene expression was specific for the miR 292-3p target sequences, and not merely a random miRNA target sequence.

In another experiment, clones containing a construct having an NL-Crei gene with four copies of an miRNA recognition sequence for miR 292-3p, miR 291a-5p, miR 1-1, or miR 294 in its 3'-UTR were tested in a similar FACS assay for GFP expression. Four clones of each were tested. Average percent GFP on FACS analysis revealed that neither clones containing the miR 291a-5p recognition sequence nor the miR 1-1 recognition sequence showed inhibition of Cre expression (percent GFP greater than or equal to 96%), whereas an average of only about 46.5% of all cells containing miR 292-3p recognition sequence, and an average of only about 37.0% of all cells containing the miR 294 recognition sequence, exhibited GFP expression.

None of the cells were selected for maintenance of pluripotency in the course of this experiment. This experiment establishes that recombinase activity can effectively be reduced by operably linking the recombinase gene to a miRNA target sequence in the 3'-UTR of the recombinase gene. These results also establish that it is possible to select for ES cells, from a mixture of cells (using FACS) that have not differentiated, e.g., that have not ceased expressing miRNAs expressed only in ES cells, or separating out cells that have ceased to express miRNAs expressed only in ES cells.

Example 6

Promoter Control of Expression: Prm1 and Blimp1

Figure 5:
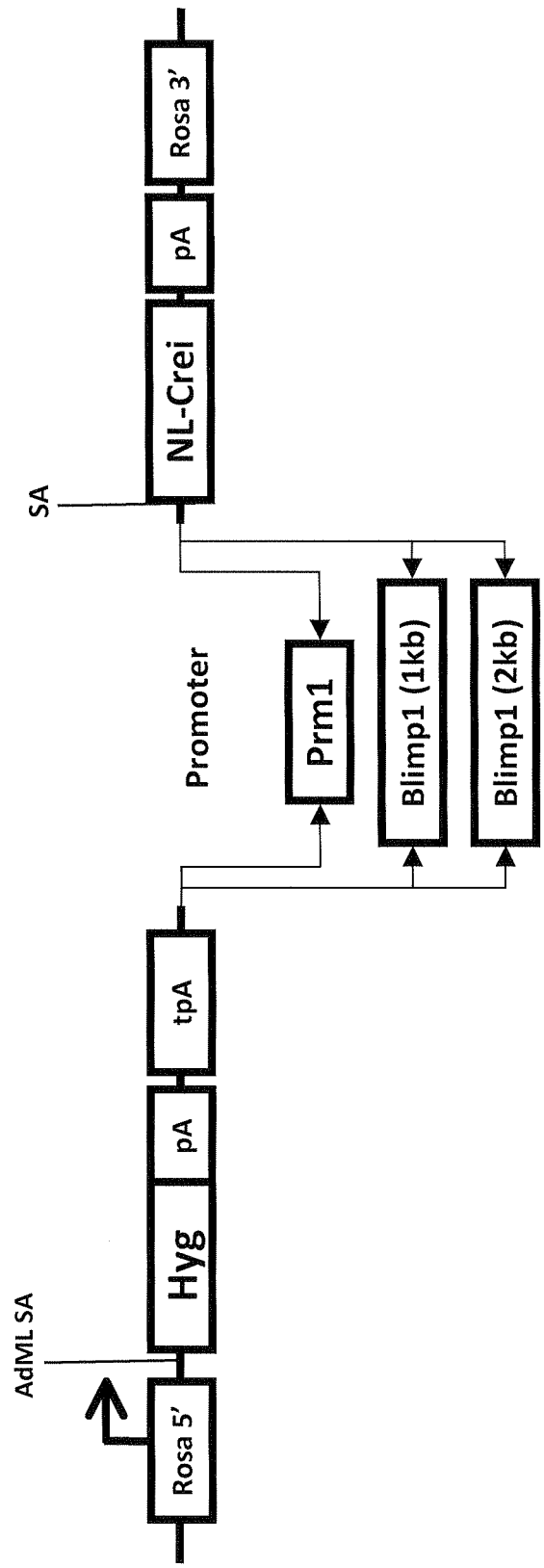
FIG. 5 illustrates a targeting vector of an embodiment of the invention that comprises a recombinase gene operably linked to a promoter that is inactive or substantially inactive in undifferentiated (e.g., ES) cells, but is active in differentiated cells.

Mouse ES cells were transfected as described above with a first construct containing a GFP gene in reverse orientation flanked by recombinase recognition sites directing an inversion (FIG. 7, Panel B), and a second construct containing a NL-Crei gene driven by either a Prm1 promoter, a Blimp1 (1 kb fragment), or a Blimp 1 (2 kb fragment) promoter (FIG. 5). Following electroporation, cells were grown in the presence of hygromycin and assayed by FACS for GFP expression. The ES cells were grown under conditions sufficient to maintain pluripotency.

Four clones having a Prm1 promoter driving Cre expression, four clones having a Blimp1 (1 kb fragment) driving Cre expression, and four clones having a Blimp1 (2 kb fragment) driving Cre expression were analyzed by phase contrast microscopy and by fluorescence microscopy to detect GFP-expressing cells. Cell counts were averaged and less than 1% of cells having the Prm1 promoter were GFP-positive, less than 0.1% of cells having the Blimp1 (1 kb fragment) promoter were GFP-positive, and less than 0.1% of cells having the Blimp1 (2 kb fragment) promoter were GFP-positive. These results establish that the Prm1 promoter and both Blimp1 promoter fragments were inactive in ES cells grown under conditions sufficient to support pluripotency. Thus, these promoters can be operably linked to a recombinase in ES cells maintained under pluripotency conditions, without any significant expression of the recombinase. Upon loss of pluripotency or differentiation, or upon activation in a germ cell, the promoters are expected to effectively drive Cre expression.

FACS analysis of ES cell clones comprising a Prm1-driven NL-Crei gene, a 1 kb Blimp1-driven NL-Crei gene, and a 2 kb Blimp1-driven NL-Crei gene supported the microscopy results described above. Essentially no GFP-expressing cells were detected in non-differentiated ES cell samples (data not shown).

One clone bearing the Blimp1 (2 kb fragment) was used as a donor ES cell to generate a mouse using the VELOCI-MOUSE® method as described above, with a Swiss Webster host embryo. E13.5 F0 generation embryos were harvested and examined for donor and host contribution. They appeared normal and genotyping results (donor cell vs. host embryo contribution) established that five embryos were essentially fully ES cell-derived (i.e., derived from the donor ES cell bearing a Blimp1 (2 kb fragment)-driven NL-Crei gene and the reverse-oriented GFP construct). Fluorescence analysis of one of the five embryos revealed a significant and apparently homogenous widespread fluorescence over background, where background was fluorescence in embryos derived wholly from host cells (i.e., embryos lacking a GFP gene). These results establish that, upon differentiation, the donor ES cells effectively drive transcription of the NL-Crei gene from the Blimp1 promoter, which produces Cre and places the inverted GFP gene in orientation for transcription, and GFP is effectively transcribed.

Consistent with the GFP fluorescence seen in embryos, genotyping of a tail biopsy from live-born mice of the same genotype as the embryos described above (with NL-Crei operably linked to a Blimp1 promoter) revealed that the embryos were mosaic with respect to the Cre-mediated rearrangement of the GFP allele; both rearranged and unrearranged alleles were detected in tail DNA of live-born mice. Blimp1 is known to drive expression in some lineages, but not others. Blimp1 is also well-known to be active in cells of male gametogenic lineage (leading to sperm). Thus, it is expected that breeding F0 mice will result in an F1 generation that exhibits uniform expression of GFP in all cells and tissues.

Genotyping of a tail biopsy from live-born mice of the same genotype as the embryos described above (with NL-Crei operably linked to a Prm1 promoter) revealed no detectable Cre-driven rearrangement of the GFP allele, as expected. The Prm1 promoter is expected to drive expression in sperm lineage cells. Thus, it is expected that breeding F0 mice will result in an F1 generation that exhibits uniform expression of GFP in all cells and tissues.

We claim:

1. A method for making a genetically modified F0 mouse, comprising:
   (a) introducing a donor mouse ES cell into a host mouse embryo, wherein the donor mouse ES cell is genetically modified to comprise:
      (i) a selection cassette that comprises a selectable marker, wherein the selection cassette is flanked upstream and downstream with recombinase recognition sites, and
      (ii) a recombinase expression cassette that comprises a recombinase gene operably linked to a Blimp1 promoter, wherein the Blimp1 promoter has the sequence comprising SEQ ID NO:2 or SEQ ID NO:3, and wherein the recombinase expression cassette is flanked upstream and downstream with the recombinase recognition sites;
   (b) implanting the host mouse embryo of step (a) into a mouse capable of gestating the host mouse embryo;
   (c) maintaining the mouse of step (b) under conditions sufficient for gestation; and,
   (d) obtaining from the mouse of step (c) a genetically modified F0 mouse that lacks a selection cassette and the recombinase expression cassette in a germ cell and retains a selection cassette and the recombinase expression cassette in a non-germ cell.

2. The method of claim 1, wherein the genetically modified mouse is a male and lacks the selection cassette and the recombinase expression cassette in its germ cells.

3. The method of claim 1, wherein the selectable marker is operably linked to a promoter that is not a Blimp1 promoter.

4. The method of claim 3, wherein the selectable marker is operably linked to a promoter selected from the group consisting of a UbC promoter, an hCMV promoter, an mCMV promoter, a CAGGS promoter, an EF1 promoter, a Pgk1 promoter, a beta-actin promoter, and a ROSA26 promoter.

5. The method of claim 3, wherein the selectable marker is a neomycin phosphotransferase (neo$^r$) gene and is operably linked to a UbC promoter.

6. The method of claim 2, further comprising: (e) breeding the genetically modified mouse to a female mouse, wherein the breeding results in progeny that lack the selection cassette and the recombinase expression cassette.

7. An F0 mouse made by a method comprising:
   (a) introducing a donor mouse ES cell into a host mouse embryo, wherein the donor mouse ES cell is genetically modified to comprise:
      (i) a selection cassette that comprises a selectable marker, wherein the selection cassette is flanked upstream and downstream with recombinase recognition sites, and
      (ii) a recombinase expression cassette that comprises a recombinase gene operably linked to a Blimp1 promoter, wherein the Blimp1 promoter has the set sequence comprising SEQ ID NO:2 or SEQ ID NO:3, and wherein the recombinase expression cassette is flanked upstream and downstream with the recombinase recognition sites;
   (b) implanting the host mouse embryo of step (a) into a mouse capable of gestating the host mouse embryo;
   (c) maintaining the host mouse of step (b) under conditions sufficient for gestation; and,
   (d) obtaining from the mouse of step (c) a genetically modified F0 mouse that lacks a selection cassette and the recombinase expression cassette in a germ cell and retains a selection cassette and the recombinase expression cassette in a non-germ cell.

8. The mouse of claim 7, wherein the genetically modified mouse is a male and lacks the selection cassette and the recombinase expression cassette in its germ cells.

9. The mouse of claim 7, wherein the selectable marker is operably linked to a promoter that is not a Blimp1 promoter.

10. The mouse of claim 9, wherein the selectable marker is operably linked to a promoter selected from the group consisting of a UbC promoter, an hCMV promoter, an mCMV promoter, a CAGGS promoter, an EF1 promoter, a Pgk1 promoter, a beta-actin promoter, and a ROSA26 promoter.

11. The mouse of claim 9, wherein the selectable marker is a neomycin phosphotransferase (neo$^r$) gene and is operably linked to a UbC promoter.

* * * * *

UNITED STATES PATENT AND TRADEMARK OFFICE
CERTIFICATE OF CORRECTION

| | | |
|---|---|---|
| PATENT NO. | : 8,946,505 B2 | Page 1 of 1 |
| APPLICATION NO. | : 13/934829 | |
| DATED | : February 3, 2015 | |
| INVENTOR(S) | : David Frendewey et al. | |

It is certified that error appears in the above-identified patent and that said Letters Patent is hereby corrected as shown below:

In the Claims,

Column 44,

In claim 7, line 11 delete "set".

In claim 7, line 18 delete "host".

Signed and Sealed this
Sixteenth Day of June, 2015

Michelle K. Lee
*Director of the United States Patent and Trademark Office*